(12) United States Patent
Kong et al.

(10) Patent No.: US 6,191,267 B1
(45) Date of Patent: Feb. 20, 2001

(54) CLONING AND PRODUCING THE N.BSTNBI NICKING ENDONUCLEASE

(75) Inventors: Huimin Kong, Wenham; Lauren S. Higgins, Essex; Michael Dalton, Manchester; Rebecca B. Kucera; Ira Schildkraut, both of Hamilton, all of MA (US)

(73) Assignee: New England Biolabs, Inc., Beverly, MA (US)

( * ) Notice: Under 35 U.S.C. 154(b), the term of this patent shall be extended for 0 days.

(21) Appl. No.: 09/586,935

(22) Filed: Jun. 2, 2000

(51) Int. Cl.[7] .......................... C07H 21/04; C12N 15/85; C12N 15/86; C12N 1/20; C12N 1/21; C12N 15/63; C12N 15/00

(52) U.S. Cl. .................... 536/23.4; 536/23.1; 435/320.1; 435/252.3; 435/69.1; 435/455; 435/471; 435/325

(58) Field of Search ................... 536/23.4, 23.1; 435/320.1, 252.3, 69.1, 455, 471, 325

(56) References Cited

U.S. PATENT DOCUMENTS

| | | | |
|---|---|---|---|
| 5,200,333 | 4/1993 | Wilson | 435/172.3 |
| 5,492,823 | 2/1996 | Xu | 435/199 |

OTHER PUBLICATIONS

Roberts and Macelis, Nucleic Acids Res. 26:338–350 (1998).
Heitman, Genetic Engineering, 15:57–107 (1993).
Kornberg and Baker, DNA Replication, 2nd edition, W.H. Freeman and Company, New York :(1992).
Geider, et al., J. Biol. Chem. 257:6488–6493 (1982).
Higashitani, et al., J. Mol. Biol. 237:388–400 (1994).
Modrich, J. Biol. Chem., 264:6597–6600 (1989).
Abdurashitov, et al., Mol. Biol. (Mosk) 30:1261–1267 (1996).
Walker, et al., Proc. Natl. Acad. Sci. USA 89:392–396 (1992).
Walker and Linn, Clin. Chem. 42:1604–1608 (1996).
Spears, et al., Anal. Biochm. 247:130–137 (1997).
Kosykh, et al. Molec. Gen. Genet. 178:717–719 (1980).
Mann, et al., Gene 3:97–112 (1978).
Walder, et al., Proc. Natl. Acad. Sci 78:1503–1507 (1981).
Bougueleret, et al., Nucl. Acids Res. 12:3659–3676 (1984).
Gingeras and Brooks, Proc. Natl. Acad. Sci. USA 80:402–406 (1983).
Theriault and Roy, Gene 19:355–359 (1982).
Blumenthal, et al., J. Bacteriol. 164:501–509 (1985).
Kiss, et al., Nucl. Acids Re. 13:6403–6421 (1985).
Szomolanyi, et al., Gene 10:219–225 (1980).
Janulaitis, et al., Gene 20:197–204 (1982).
Kiss and Baldauf, Gene 21:111–119 (1983).
Walder, et al., J. Biol. Chem. 258:1235–1241 (1983).
Piekarowicz, et al., Nucleic Acids Res. 19:1831–1835 (1991).
Piekarowicz, et al., J. Bacteriology 173:150–155 (1991).
Fomenkov, et al. Nucleic Acids Res. 22:2399–2403 (1994).
Lunnen, et al., Gene 74:25–32 (1988).
Raleigh and Wilson, Proc. Natl. Acad. Sci. USA 83:9070–9074 (1986).
Heitman and Model, J. Bacteriology 196:3243–3250 (1987).
Raleigh, et al., Genetics 122:279–296 (1989).
Waitee–Rees, et al., J. Bacteriology, 173:5207–5219 (1991).
Ochman, et al., Genetics, 120:621 (1988).
Triglia, et al., Nucl. Acids Res. 16:8186 (1988).
Silver and Keerikatte, J. Cell. Biochem. (Suppl) 13E:306, Abstract No. WH239 (1989).
Matsudaira, J. Biol. Chem. 262:10035–10038 (1987).
Looney, et al., Gene 80:193–208 (1989).

*Primary Examiner*—Jeffrey Fredman
*Assistant Examiner*—Juliet C. Einsmann
(74) *Attorney, Agent, or Firm*—Gregory D. Williams

(57) ABSTRACT

The present invention relates to recombinant DNA which encodes a novel nicking endonuclease, N.BstNBI, and the production of N.BstNBI restriction endonuclease from the recombinant DNA utilizing PleI modification methylase. Related expression vectors, as well as the application of N.BstNBI in non-thio strand displacement amplification, is disclosed also.

5 Claims, 11 Drawing Sheets

```
5'-NNNNNNGAGTCNNNNNNNN-3'        (SEQ ID NO:1)
3'-NNNNNNCTCAGNNNNNNNN-5'
```

```
5'-NNNNNNGAGTCNNNNNNNN-3'    (SEQ ID NO:1)
3'-NNNNNNCTCAGNNNNNNNN-5'
```

R 1815 bp n.bstNBIR — ORF1 — M 906 bp n.bstNBIM

FIG. 2A

```
          10                  30                  50
ATGGCTAAAAAAGTTAATTGGTATGTTTCTTGTTCACCTAGAAGTCCAGAAAAAATTCAG
MetAlaLysLysValAsnTrpTyrValSerCysSerProArgSerProGluLysIleGln 70                  90                 110
CCTGAGTTAAAAGTACTAGCAAATTTTGAGGGAAGTTATTGGAAAGGGGTAAAAGGGTAT
ProGluLeuLysValLeuAlaAsnPheGluGlySerTyrTrpLysGlyValLysGlyTyr 130                 150                 170
AAAGCACAAGAGGCATTTGCTAAAGAACTTGCTGCTTTACCACAATTCTTAGGTACTACT
LysAlaGlnGluAlaPheAlaLysGluLeuAlaAlaLeuProGlnPheLeuGlyThrThr 190                 210                 230
TATAAAAAAGAAGCTGCATTTTCTACTCGAGACAGAGTGGCACCAATGAAAACTTATGGT
TyrLysLysGluAlaAlaPheSerThrArgAspArgValAlaProMetLysThrTyrGly 250                 270                 290
TTCGTATTTGTAGATGAAGAAGGTTATCTTCGTATAACTGAAGCAGGGAAAATGCTTGCA
PheValPheValAspGluGluGlyTyrLeuArgIleThrGluAlaGlyLysMetLeuAla 310                 330                 350
AATAACCGAAGACCCAAAGATGTTTTCTTAAAAACAGTTAGTAAAGTGGCAATATCCATCG
AsnAsnArgArgProLysAspValPheLeuLysGlnLeuValLysTrpGlnTyrProSer 370                 390                 410
TTTCAACACAAAGGTAAGGAATATCCCGAGGAGGAATGGAGTATAAATCCTCTTGTATTT
PheGlnHisLysGlyLysGluTyrProGluGluGluTrpSerIleAsnProLeuValPhe 430                 450                 470
GTTCTTAGCTTACTAAAAAAGGTAGGCGGCCTCAGTAAATTAGATATTGCTATGTTCTGT
ValLeuSerLeuLeuLysLysValGlyGlyLeuSerLysLeuAspIleAlaMetPheCys 490                 510                 530
TTAACAGCAACAAATAATAATCAGGTGGATGAAATTGCAGAGGAAATAATGCAGTTCCGT
LeuThrAlaThrAsnAsnGlnValAspGluIleAlaGluGluIleMetGlnPheArg 550                 570                 590
AATGAACGTGAAAAAATAAAAGGACAAAATAAGAAACTTGAGTTTACTGAGAATTACTTT
AsnGluArgGluLysIleLysGlyGlnAsnLysLysLeuGluPheThrGluAsnTyrPhe 610                 630                 650
TTTAAAAGATTCGAAAAGATTTATGGAAATGTAGGTAAAATTCGTGAAGGGAAATCTGAC
PheLysArgPheGluLysIleTyrGlyAsnValGlyLysIleArgGluGlyLysSerAsp 670                 690                 710
TCTTCACATAAGTCAAAAATTGAAACTAAAATGAGAAATGCACGAGATGTGGCAGATGCA
SerSerHisLysSerLysIleGluThrLysMetArgAsnAlaArgAspValAlaAspAla 730                 750                 770
ACCACAAGATATTTTCGATATACAGGTCTATTTGTTGCAAGAGGGAATCAACTCGTCTTA
ThrThrArgTyrPheArgTyrThrGlyLeuPheValAlaArgGlyAsnGlnLeuValLeu
```

FIG. 2B

```
       790              810                  830
AATCCAGAAAAATCTGATTTAATTGATGAAATTATCAGTTCATCAAAAGTTGTAAAGAAC
AsnProGluLysSerAspLeuIleAspGluIleIleSerSerSerLysValValLysAsn 850              870                  890
TATACGAGAGTAGAGGAATTTCATGAATATTATGGAAATCCGAGTTTACCACAGTTTTCA
TyrThrArgValGluGluPheHisGluTyrTyrGlyAsnProSerLeuProGlnPheSer 910              930                  950
TTTGAGACAAAAGAGCAACTTTTAGATCTAGCCCATAGAATACGAGATGAAAATACCAGA
PheGluThrLysGluGlnLeuLeuAspLeuAlaHisArgIleArgAspGluAsnThrArg 970              990                 1010
CTAGCTGAGCAATTAGTAGAACATTTTCCAAATGTTAAAGTTGAAATACAAGTCCTTGAA
LeuAlaGluGlnLeuValGluHisPheProAsnValLysValGluIleGlnValLeuGlu 1030             1050                 1070
GACATTTATAATTCTCTTAATAAAAAAGTTGATGTAGAAACATTAAAAGATGTTATTTAC
AspIleTyrAsnSerLeuAsnLysLysValAspValGluThrLeuLysAspValIleTyr 1090             1110                 1130
CATGCTAAGGAATTACAGCTAGAACTCAAAAAGAAAAAGTTACAAGCAGATTTTAATGAC
HisAlaLysGluLeuGlnLeuGluLeuLysLysLysLysLeuGlnAlaAspPheAsnAsp 1150             1170                 1190
CCACGTCAACTTGAAGAAGTCATTGACCTTCTTGAGGTATATCATGAGAAAAAGAATGTG
ProArgGlnLeuGluGluValIleAspLeuLeuGluValTyrHisGluLysLysAsnVal 1210             1230                 1250
ATTGAAGAGAAAATTAAAGCTCGCTTCATTGCAAATAAAAATACTGTATTTGAATGGCTT
IleGluGluLysIleLysAlaArgPheIleAlaAsnLysAsnThrValPheGluTrpLeu 1270             1290                 1310
ACGTGGAATGGCTTCATTATTCTTGGAAATGCTTTAGAATATAAAAACAACTTCGTTATT
ThrTrpAsnGlyPheIleIleLeuGlyAsnAlaLeuGluTyrLysAsnAsnPheValIle 1330             1350                 1370
GATGAAGAGTTACAACCAGTTACTCATGCCGCAGGTAACCAGCCTGATATGGAAATTATA
AspGluGluLeuGlnProValThrHisAlaAlaGlyAsnGlnProAspMetGluIleIle 1390             1410                 1430
TATGAAGACTTTATTGTTCTTGGTGAAGTAACAACTTCTAAGGGAGCAACCCAGTTTAAG
TyrGluAspPheIleValLeuGlyGluValThrThrSerLysGlyAlaThrGlnPheLys 1450             1470                 1490
ATGGAATCAGAACCAGTAACAAGGCATTATTTAAACAAGAAAAAAGAATTAGAAAAGCAA
MetGluSerGluProValThrArgHisTyrLeuAsnLysLysLysGluLeuGluLysGln 1510             1530                 1550
GGAGTAGAGAAAGAACTATATTGTTTATTCATTGCGCCAGAAATCAATAAGAATACTTTT
GlyValGluLysGluLeuTyrCysLeuPheIleAlaProGluIleAsnLysAsnThrPhe
```

FIG. 2C

```
         1570                1590                 1610
GAGGAGTTTATGAAATACAATATTGTTCAAAACACAAGAATTATCCCTCTCTCATTAAAA
GluGluPheMetLysTyrAsnIleValGlnAsnThrArgIleIleProLeuSerLeuLys 1630                1650                 1670
CAGTTTAACATGCTCCTAATGGTACAGAAGAAATTAATTGAAAAAGGAAGAAGGTTATCT
GlnPheAsnMetLeuLeuMetValGlnLysLysLeuIleGluLysGlyArgArgLeuSer 1690                1710                 1730
TCTTATGATATTAAGAATCTGATGGTCTCATTATATCGAACAACTATAGAGTGTGAAAGA
SerTyrAspIleLysAsnLeuMetValSerLeuTyrArgThrThrIleGluCysGluArg 1750                1770                 1790
AAATATACTCAAATTAAAGCTGGTTTAGAAGAAACTTTAAATAATTGGGTTGTTGACAAG
LysTyrThrGlnIleLysAlaGlyLeuGluGluThrLeuAsnAsnTrpValValAspLys

1810
GAGGTAAGGTTTTAA
GluValArgPheEnd
```

FIG. 3A

```
         10                      30                         50
ATGAAACCTATTTTAAAATATCGTGGTGGAAAAAAAGCAGAAATTCCTTTCTTTATTGAC
MetLysProIleLeuLysTyrArgGlyGlyLysLysAlaGluIleProPhePheIleAsp 70                      90                        110
CATATACCCAATGATATCGAAACCTACTTTGAACCCTTTGTCGGGGGTGGTGCTGTATTC
HisIleProAsnAspIleGluThrTyrPheGluProPheValGlyGlyGlyAlaValPhe 130                     150                        170
TTCCATTTAGAACATGAAAAATCAGTTATCAATGATATTAATTCTAAGCTTTATAAGTTC
PheHisLeuGluHisGluLysSerValIleAsnAspIleAsnSerLysLeuTyrLysPhe 190                     210                        230
TATCTTCAATTAAAGCACAATTTTGATGAGGTAACTAAACAATTAAACGAACTACAGGAA
TyrLeuGlnLeuLysHisAsnPheAspGluValThrLysGlnLeuAsnGluLeuGlnGlu 250                     270                        290
ATATATGAAAAAAACCAAAAGGAATATGAGGAAAAAAAAGCTCTTGCTCCTGCTGGTGTC
IleTyrGluLysAsnGlnLysGluTyrGluGluLysLysAlaLeuAlaProAlaGlyVal 310                     330                        350
AGAGTGGAAAATAAAAATGAAGAACTATATTATGAGCTAAGGAACGAATTTAACTATCCA
ArgValGluAsnLysAsnGluGluLeuTyrTyrGluLeuArgAsnGluPheAsnTyrPro 370                     390                        410
TCAGGAAAATGGCTAGACGCAGTAATTTATTATTTTATAAATAAAACTGCTTATAGTGGG
SerGlyLysTrpLeuAspAlaValIleTyrTyrPheIleAsnLysThrAlaTyrSerGly 430                     450                        470
ATGATAAGGTATAACAGTAAAGGAGAATATAACGTTCCTTTTGGAAGATACAAAAACTTT
MetIleArgTyrAsnSerLysGlyGluTyrAsnValProPheGlyArgTyrLysAsnPhe 490                     510                        530
AATACAAAAATCATTACTAAACAACACCATAACCTGCTTCAAAAAACAGAAATATATAAT
AsnThrLysIleIleThrLysGlnHisHisAsnLeuLeuGlnLysThrGluIleTyrAsn 550                     570                        590
AAAGATTTTTCTGAAATTTTTAAGATGGCAAAACCAAATGACTTCATGTTTCTTGATCCT
LysAspPheSerGluIlePheLysMetAlaLysProAsnAspPheMetPheLeuAspPro 610                     630                        650
CCATATGATTGTATTTTTAGTGATTATGGAAATATGGAGTTTACAGGTGATTTCGACGAG
ProTyrAspCysIlePheSerAspTyrGlyAsnMetGluPheThrGlyAspPheAspGlu 670                     690                        710
AGGGAACATCGTAGGCTTGCTGAAGAGTTTAAAAACTTAAAGTGCCGTGCACTAATGATC
ArgGluHisArgArgLeuAlaGluGluPheLysAsnLeuLysCysArgAlaLeuMetIle 730                     750                        770
ATTAGTAAAACGGAATTAACTACCGAACTATATAAAGATTATATCGTTGATGAATATCAT
IleSerLysThrGluLeuThrThrGluLeuTyrLysAspTyrIleValAspGluTyrHis
```

FIG. 3B

```
        790               810                830
AAAAGCTATTCTGTAAACATTAGAAATAGATTTAAGAATGAAGCAAAGCATTATATAATC
LysSerTyrSerValAsnIleArgAsnArgPheLysAsnGluAlaLysHisTyrIleIle 850               870                890
AAGAACTATGATTATGTACGAAAAAATAAAGAAGAAAAATATGAGCAACTTGAACTTATT
LysAsnTyrAspTyrValArgLysAsnLysGluGluLysTyrGluGlnLeuGluLeuIle

CATTAG
HisEnd
```

FIG. 4A

```
        10                    30                   50
ATGAAGCCATTAGTTAAATATAGAGGTGGAAAGTCTAAGGAAATTCCATATCTAATTAAA
MetLysProLeuValLysTyrArgGlyGlyLysSerLysGluIleProTyrLeuIleLys 70                    90                  110
CATATCCCTGAATTTAAAGGGCGCTACATAGAGCCTTTTTTTGGTGGGGGGGCTTTATTT
HisIleProGluPheLysGlyArgTyrIleGluProPhePheGlyGlyGlyAlaLeuPhe 130                   150                  170
TTTTATATAGAGCCAGAAAAATCTATTATCAATGACATTAATAAAAAACTTATAGATTTT
PheTyrIleGluProGluLysSerIleIleAsnAspIleAsnLysLysLeuIleAspPhe 190                   210                  230
TATCGAGATGTTAAAGATAACTTTGTTCAATTGCGTCATGAGCTTGATGAGATAGAATGT
TyrArgAspValLysAspAsnPheValGlnLeuArgHisGluLeuAspGluIleGluCys 250                   270                  290
ATTTATGAAAAGAATAGAGTTGAATACGAAACTAGAAAGAAATTAAATCCTACTGAACGT
IleTyrGluLysAsnArgValGluTyrGluThrArgLysLysLeuAsnProThrGluArg 310                   330                  350
GTAGATGATGGAAATGAAGATTTCTATTACTTCATGAGGAATGAATTCAATAAAGATTTT
ValAspAspGlyAsnGluAspPheTyrTyrPheMetArgAsnGluPheAsnLysAspPhe 370                   390                  410
TCGGATAGATATCTTTCATCAACACTGTATTTTTATATAAATAAGACTGCGTACTCTGGA
SerAspArgTyrLeuSerSerThrLeuTyrPheTyrIleAsnLysThrAlaTyrSerGly 430                   450                  470
ATGATTAGATATAACTCAAAAGGTGAGTTTAATGTTCCGTTTGGTAGATATAAAAATCTC
MetIleArgTyrAsnSerLysGlyGluPheAsnValProPheGlyArgTyrLysAsnLeu 490                   510                  530
AATACAAAACTTGTGGCTAATGAACATCACTTGTTAATGCAGGGTGCTCAGATATTTAAT
AsnThrLysLeuValAlaAsnGluHisHisLeuLeuMetGlnGlyAlaGlnIlePheAsn 550                   570                  590
GAAGATTACAGCGAGATCTTCAAGATGGCGAGAAAAGATGATTTTATATTTCTAGACCCT
GluAspTyrSerGluIlePheLysMetAlaArgLysAspAspPheIlePheLeuAspPro 610                   630                  650
CCCTATGATTGCGTATTTAGTGATTATGGTAATGAGGAATATAAAGATGGTTTCAATGTA
ProTyrAspCysValPheSerAspTyrGlyAsnGluGluTyrLysAspGlyPheAsnVal 670                   690                  710
GATGCTCATGTGAAATTGAGTGAGGACTTTAAGAAATTGAAATGCAAAGCCATGATGGTT
AspAlaHisValLysLeuSerGluAspPheLysLysLeuLysCysLysAlaMetMetVal 730                   750                  770
ATCGGTAAGACTGAATTGACTGATGGGTTGTATAAGAAAATGATTATTGATGAATACGAT
IleGlyLysThrGluLeuThrAspGlyLeuTyrLysLysMetIleIleAspGluTyrAsp
```

FIG. 4B

```
     790              810                830
AAAAGTTATTCTGTGAATATAAGGAATAGATTTAAGTCTGTTGCAAAGCATATAGTTGTT
LysSerTyrSerValAsnIleArgAsnArgPheLysSerValAlaLysHisIleValVal

850
GCAAATTATTGA
AlaAsnTyrEnd
```

(SEQ ID NO: 8)

SEQUENCE LISTING

<160> NUMBER OF SEQ ID NOS: 27

<210> SEQ ID NO 1
<211> LENGTH: 19
<212> TYPE: DNA
<213> ORGANISM: Bacillus stearothermophilus
<220> FEATURE:
<223> OTHER INFORMATION: At position 1-6 and 12-19, N=G, A, C, or T(U)

<400> SEQUENCE: 1
nnnnnngagt cnnnnnnnn                                                    19

<210> SEQ ID NO 2
<211> LENGTH: 1815
<212> TYPE: DNA
<213> ORGANISM: Bacillus stearothermophilus
<220> FEATURE:
<221> NAME/KEY: CDS
<222> LOCATION: (1)..(1812)

<400> SEQUENCE: 2

```
atg gct aaa aaa gtt aat tgg tat gtt tct tgt tca cct aga agt cca       48
Met Ala Lys Lys Val Asn Trp Tyr Val Ser Cys Ser Pro Arg Ser Pro
 1               5                  10                  15 gaa aaa att cag cct gag tta aaa gta cta gca aat ttt gag gga agt       96
Glu Lys Ile Gln Pro Glu Leu Lys Val Leu Ala Asn Phe Glu Gly Ser
             20                  25                  30 tat tgg aaa ggg gta aaa ggg tat aaa gca caa gag gca ttt gct aaa      144
Tyr Trp Lys Gly Val Lys Gly Tyr Lys Ala Gln Glu Ala Phe Ala Lys
         35                  40                  45 gaa ctt gct gct tta cca caa ttc tta ggt act act tat aaa aaa gaa      192
Glu Leu Ala Ala Leu Pro Gln Phe Leu Gly Thr Thr Tyr Lys Lys Glu
     50                  55                  60 gct gca ttt tct act cga gac aga gtg gca cca atg aaa act tat ggt      240
Ala Ala Phe Ser Thr Arg Asp Arg Val Ala Pro Met Lys Thr Tyr Gly
 65                  70                  75                  80 ttc gta ttt gta gat gaa gaa ggt tat ctt cgt ata act gaa gca ggg      288
Phe Val Phe Val Asp Glu Glu Gly Tyr Leu Arg Ile Thr Glu Ala Gly
                 85                  90                  95 aaa atg ctt gca aat aac cga aga ccc aaa gat gtt ttc tta aaa cag      336
Lys Met Leu Ala Asn Asn Arg Arg Pro Lys Asp Val Phe Leu Lys Gln
            100                 105                 110 tta gta aag tgg caa tat cca tcg ttt caa cac aaa ggt aag gaa tat      384
Leu Val Lys Trp Gln Tyr Pro Ser Phe Gln His Lys Gly Lys Glu Tyr
        115                 120                 125 ccc gag gag gaa tgg agt ata aat cct ctt gta ttt gtt ctt agc tta      432
Pro Glu Glu Glu Trp Ser Ile Asn Pro Leu Val Phe Val Leu Ser Leu
    130                 135                 140 cta aaa aag gta ggc ggc ctc agt aaa tta gat att gct atg ttc tgt      480
Leu Lys Lys Val Gly Gly Leu Ser Lys Leu Asp Ile Ala Met Phe Cys
```

-continued

```
                145                 150                 155                 160
tta aca gca aca aat aat aat cag gtg gat gaa att gca gag gaa ata         528
Leu Thr Ala Thr Asn Asn Asn Gln Val Asp Glu Ile Ala Glu Glu Ile
                    165                 170                 175 atg cag ttc cgt aat gaa cgt gaa aaa ata aaa gga caa aat aag aaa         576
Met Gln Phe Arg Asn Glu Arg Glu Lys Ile Lys Gly Gln Asn Lys Lys
                180                 185                 190 ctt gag ttt act gag aat tac ttt ttt aaa aga ttc gaa aag att tat         624
Leu Glu Phe Thr Glu Asn Tyr Phe Phe Lys Arg Phe Glu Lys Ile Tyr
            195                 200                 205 gga aat gta ggt aaa att cgt gaa ggg aaa tct gac tct tca cat aag         672
Gly Asn Val Gly Lys Ile Arg Glu Gly Lys Ser Asp Ser Ser His Lys
        210                 215                 220 tca aaa att gaa act aaa atg aga aat gca cga gat gtg gca gat gca         720
Ser Lys Ile Glu Thr Lys Met Arg Asn Ala Arg Asp Val Ala Asp Ala
225                 230                 235                 240 acc aca aga tat ttt cga tat aca ggt cta ttt gtt gca aga ggg aat         768
Thr Thr Arg Tyr Phe Arg Tyr Thr Gly Leu Phe Val Ala Arg Gly Asn
                245                 250                 255 caa ctc gtc tta aat cca gaa aaa tct gat tta att gat gaa att atc         816
Gln Leu Val Leu Asn Pro Glu Lys Ser Asp Leu Ile Asp Glu Ile Ile
            260                 265                 270 agt tca tca aaa gtt gta aag aac tat acg aga gta gag gaa ttt cat         864
Ser Ser Ser Lys Val Val Lys Asn Tyr Thr Arg Val Glu Glu Phe His
        275                 280                 285 gaa tat tat gga aat ccg agt tta cca cag ttt tca ttt gag aca aaa         912
Glu Tyr Tyr Gly Asn Pro Ser Leu Pro Gln Phe Ser Phe Glu Thr Lys
    290                 295                 300 gag caa ctt tta gat cta gcc cat aga ata cga gat gaa aat acc aga         960
Glu Gln Leu Leu Asp Leu Ala His Arg Ile Arg Asp Glu Asn Thr Arg
305                 310                 315                 320 cta gct gag caa tta gta gaa cat ttt cca aat gtt aaa gtt gaa ata        1008
Leu Ala Glu Gln Leu Val Glu His Phe Pro Asn Val Lys Val Glu Ile
                325                 330                 335 caa gtc ctt gaa gac att tat aat tct ctt aat aaa aaa gtt gat gta        1056
Gln Val Leu Glu Asp Ile Tyr Asn Ser Leu Asn Lys Lys Val Asp Val
            340                 345                 350 gaa aca tta aaa gat gtt att tac cat gct aag gaa tta cag cta gaa        1104
Glu Thr Leu Lys Asp Val Ile Tyr His Ala Lys Glu Leu Gln Leu Glu
        355                 360                 365 ctc aaa aag aaa aag tta caa gca gat ttt aat gac cca cgt caa ctt        1152
Leu Lys Lys Lys Lys Leu Gln Ala Asp Phe Asn Asp Pro Arg Gln Leu
    370                 375                 380 gaa gaa gtc att gac ctt ctt gag gta tat cat gag aaa aag aat gtg        1200
Glu Glu Val Ile Asp Leu Leu Glu Val Tyr His Glu Lys Lys Asn Val
385                 390                 395                 400 att gaa gag aaa att aaa gct cgc ttc att gca aat aaa aat act gta        1248
Ile Glu Glu Lys Ile Lys Ala Arg Phe Ile Ala Asn Lys Asn Thr Val
                405                 410                 415 ttt gaa tgg ctt acg tgg aat ggc ttc att att ctt gga aat gct tta        1296
Phe Glu Trp Leu Thr Trp Asn Gly Phe Ile Ile Leu Gly Asn Ala Leu
            420                 425                 430 gaa tat aaa aac aac ttc gtt att gat gag gag tta caa cca gtt act        1344
Glu Tyr Lys Asn Asn Phe Val Ile Asp Glu Glu Leu Gln Pro Val Thr
        435                 440                 445 cat gcc gca ggt aac cag cct gat atg gaa att ata tat gaa gac ttt        1392
His Ala Ala Gly Asn Gln Pro Asp Met Glu Ile Ile Tyr Glu Asp Phe
    450                 455                 460 att gtt ctt ggt gaa gta aca act tct aag gga gca acc cag ttt aag        1440
```

```
Ile Val Leu Gly Glu Val Thr Thr Ser Lys Gly Ala Thr Gln Phe Lys
465                 470                 475                 480 atg gaa tca gaa cca gta aca agg cat tat tta aac aag aaa aaa gaa       1488
Met Glu Ser Glu Pro Val Thr Arg His Tyr Leu Asn Lys Lys Lys Glu
                    485                 490                 495 tta gaa aag caa gga gta gag aaa gaa cta tat tgt tta ttc att gcg       1536
Leu Glu Lys Gln Gly Val Glu Lys Glu Leu Tyr Cys Leu Phe Ile Ala
                500                 505                 510 cca gaa atc aat aag aat act ttt gag gag ttt atg aaa tac aat att       1584
Pro Glu Ile Asn Lys Asn Thr Phe Glu Glu Phe Met Lys Tyr Asn Ile
            515                 520                 525 gtt caa aac aca aga att atc cct ctc tca tta aaa cag ttt aac atg       1632
Val Gln Asn Thr Arg Ile Ile Pro Leu Ser Leu Lys Gln Phe Asn Met
        530                 535                 540 ctc cta atg gta cag aag aaa tta att gaa aaa gga aga agg tta tct       1680
Leu Leu Met Val Gln Lys Lys Leu Ile Glu Lys Gly Arg Arg Leu Ser
545                 550                 555                 560 tct tat gat att aag aat ctg atg gtc tca tta tat cga aca act ata       1728
Ser Tyr Asp Ile Lys Asn Leu Met Val Ser Leu Tyr Arg Thr Thr Ile
                565                 570                 575 gag tgt gaa aga aaa tat act caa att aaa gct ggt tta gaa gaa act       1776
Glu Cys Glu Arg Lys Tyr Thr Gln Ile Lys Ala Gly Leu Glu Glu Thr
                580                 585                 590 tta aat aat tgg gtt gtt gac aag gag gta agg ttt taa                   1815
Leu Asn Asn Trp Val Val Asp Lys Glu Val Arg Phe
            595                 600

<210> SEQ ID NO 3
<211> LENGTH: 604
<212> TYPE: PRT
<213> ORGANISM: Bacillus stearothermophilus

<400> SEQUENCE: 3

Met Ala Lys Lys Val Asn Trp Tyr Val Ser Cys Ser Pro Arg Ser Pro
1               5                   10                  15

Glu Lys Ile Gln Pro Glu Leu Lys Val Leu Ala Asn Phe Glu Gly Ser
                20                  25                  30

Tyr Trp Lys Gly Val Lys Gly Tyr Lys Ala Gln Glu Ala Phe Ala Lys
            35                  40                  45

Glu Leu Ala Ala Leu Pro Gln Phe Leu Gly Thr Thr Tyr Lys Lys Glu
        50                  55                  60

Ala Ala Phe Ser Thr Arg Asp Arg Val Ala Pro Met Lys Thr Tyr Gly
65                  70                  75                  80

Phe Val Phe Val Asp Glu Glu Gly Tyr Leu Arg Ile Thr Glu Ala Gly
                85                  90                  95

Lys Met Leu Ala Asn Asn Arg Arg Pro Lys Asp Val Phe Leu Lys Gln
            100                 105                 110

Leu Val Lys Trp Gln Tyr Pro Ser Phe Gln His Lys Gly Lys Glu Tyr
        115                 120                 125

Pro Glu Glu Glu Trp Ser Ile Asn Pro Leu Val Phe Val Leu Ser Leu
    130                 135                 140

Leu Lys Lys Val Gly Gly Leu Ser Lys Leu Asp Ile Ala Met Phe Cys
145                 150                 155                 160

Leu Thr Ala Thr Asn Asn Gln Val Asp Glu Ile Ala Glu Glu Ile
                165                 170                 175

Met Gln Phe Arg Asn Glu Arg Glu Lys Ile Lys Gly Gln Asn Lys Lys
            180                 185                 190
```

-continued

```
Leu Glu Phe Thr Glu Asn Tyr Phe Lys Arg Phe Glu Lys Ile Tyr
        195                 200                 205
Gly Asn Val Gly Lys Ile Arg Glu Gly Lys Ser Asp Ser Ser His Lys
    210                 215                 220
Ser Lys Ile Glu Thr Lys Met Arg Asn Ala Arg Asp Val Ala Asp Ala
225                 230                 235                 240
Thr Thr Arg Tyr Phe Arg Tyr Thr Gly Leu Phe Val Ala Arg Gly Asn
                245                 250                 255
Gln Leu Val Leu Asn Pro Glu Lys Ser Asp Leu Ile Asp Glu Ile Ile
            260                 265                 270
Ser Ser Ser Lys Val Val Lys Asn Tyr Thr Arg Val Glu Glu Phe His
        275                 280                 285
Glu Tyr Tyr Gly Asn Pro Ser Leu Pro Gln Phe Ser Phe Glu Thr Lys
    290                 295                 300
Glu Gln Leu Leu Asp Leu Ala His Arg Ile Arg Asp Glu Asn Thr Arg
305                 310                 315                 320
Leu Ala Glu Gln Leu Val Glu His Phe Pro Asn Val Lys Val Glu Ile
                325                 330                 335
Gln Val Leu Glu Asp Ile Tyr Asn Ser Leu Asn Lys Lys Val Asp Val
            340                 345                 350
Glu Thr Leu Lys Asp Val Ile Tyr His Ala Lys Glu Leu Gln Leu Glu
        355                 360                 365
Leu Lys Lys Lys Lys Leu Gln Ala Asp Phe Asn Asp Pro Arg Gln Leu
    370                 375                 380
Glu Glu Val Ile Asp Leu Leu Glu Val Tyr His Glu Lys Lys Asn Val
385                 390                 395                 400
Ile Glu Glu Lys Ile Lys Ala Arg Phe Ile Ala Asn Lys Asn Thr Val
                405                 410                 415
Phe Glu Trp Leu Thr Trp Asn Gly Phe Ile Ile Leu Gly Asn Ala Leu
            420                 425                 430
Glu Tyr Lys Asn Asn Phe Val Ile Asp Glu Glu Leu Gln Pro Val Thr
        435                 440                 445
His Ala Ala Gly Asn Gln Pro Asp Met Glu Ile Ile Tyr Glu Asp Phe
    450                 455                 460
Ile Val Leu Gly Glu Val Thr Thr Ser Lys Gly Ala Thr Gln Phe Lys
465                 470                 475                 480
Met Glu Ser Glu Pro Val Thr Arg His Tyr Leu Asn Lys Lys Lys Glu
                485                 490                 495
Leu Glu Lys Gln Gly Val Glu Lys Glu Leu Tyr Cys Leu Phe Ile Ala
            500                 505                 510
Pro Glu Ile Asn Lys Asn Thr Phe Glu Glu Phe Met Lys Tyr Asn Ile
        515                 520                 525
Val Gln Asn Thr Arg Ile Ile Pro Leu Ser Leu Lys Gln Phe Asn Met
    530                 535                 540
Leu Leu Met Val Gln Lys Lys Leu Ile Glu Lys Gly Arg Arg Leu Ser
545                 550                 555                 560
Ser Tyr Asp Ile Lys Asn Leu Met Val Ser Leu Tyr Arg Thr Thr Ile
                565                 570                 575
Glu Cys Glu Arg Lys Tyr Thr Gln Ile Lys Ala Gly Leu Glu Glu Thr
            580                 585                 590
Leu Asn Asn Trp Val Val Asp Lys Glu Val Arg Phe
        595                 600
```

```
<210> SEQ ID NO 4
<211> LENGTH: 906
<212> TYPE: DNA
<213> ORGANISM: Bacillus stearothermophilus
<220> FEATURE:
<221> NAME/KEY: CDS
<222> LOCATION: (1)..(903)

<400> SEQUENCE: 4
```

| | | | | | | | | | | | | | | | | |
|---|---|---|---|---|---|---|---|---|---|---|---|---|---|---|---|---|
| atg | aaa | cct | att | tta | aaa | tat | cgt | ggt | gga | aaa | aaa | gca | gaa | att | cct | 48 |
| Met | Lys | Pro | Ile | Leu | Lys | Tyr | Arg | Gly | Gly | Lys | Lys | Ala | Glu | Ile | Pro | |
| 1 | | | | 5 | | | | | 10 | | | | | 15 | | |
| ttc | ttt | att | gac | cat | ata | ccc | aat | gat | atc | gaa | acc | tac | ttt | gaa | ccc | 96 |
| Phe | Phe | Ile | Asp | His | Ile | Pro | Asn | Asp | Ile | Glu | Thr | Tyr | Phe | Glu | Pro | |
| | | | 20 | | | | | 25 | | | | | 30 | | | |
| ttt | gtc | ggg | ggt | ggt | gct | gta | ttc | ttc | cat | tta | gaa | cat | gaa | aaa | tca | 144 |
| Phe | Val | Gly | Gly | Gly | Ala | Val | Phe | Phe | His | Leu | Glu | His | Glu | Lys | Ser | |
| | | 35 | | | | | 40 | | | | | 45 | | | | |
| gtt | atc | aat | gat | att | aat | tct | aag | ctt | tat | aag | ttc | tat | ctt | caa | tta | 192 |
| Val | Ile | Asn | Asp | Ile | Asn | Ser | Lys | Leu | Tyr | Lys | Phe | Tyr | Leu | Gln | Leu | |
| 50 | | | | | 55 | | | | | 60 | | | | | | |
| aag | cac | aat | ttt | gat | gag | gta | act | aaa | caa | tta | aac | gaa | cta | cag | gaa | 240 |
| Lys | His | Asn | Phe | Asp | Glu | Val | Thr | Lys | Gln | Leu | Asn | Glu | Leu | Gln | Glu | |
| 65 | | | | | 70 | | | | | 75 | | | | | 80 | |
| ata | tat | gaa | aaa | aac | caa | aag | gaa | tat | gag | gaa | aaa | aaa | gct | ctt | gct | 288 |
| Ile | Tyr | Glu | Lys | Asn | Gln | Lys | Glu | Tyr | Glu | Glu | Lys | Lys | Ala | Leu | Ala | |
| | | | | 85 | | | | | 90 | | | | | 95 | | |
| cct | gct | ggt | gtc | aga | gtg | gaa | aat | aaa | aat | gaa | gaa | cta | tat | tat | gag | 336 |
| Pro | Ala | Gly | Val | Arg | Val | Glu | Asn | Lys | Asn | Glu | Glu | Leu | Tyr | Tyr | Glu | |
| | | | 100 | | | | | 105 | | | | | 110 | | | |
| cta | agg | aac | gaa | ttt | aac | tat | cca | tca | gga | aaa | tgg | cta | gac | gca | gta | 384 |
| Leu | Arg | Asn | Glu | Phe | Asn | Tyr | Pro | Ser | Gly | Lys | Trp | Leu | Asp | Ala | Val | |
| | | 115 | | | | | 120 | | | | | 125 | | | | |
| att | tat | tat | ttt | ata | aat | aaa | act | gct | tat | agt | ggg | atg | ata | agg | tat | 432 |
| Ile | Tyr | Tyr | Phe | Ile | Asn | Lys | Thr | Ala | Tyr | Ser | Gly | Met | Ile | Arg | Tyr | |
| | 130 | | | | | 135 | | | | | 140 | | | | | |
| aac | agt | aaa | gga | gaa | tat | aac | gtt | cct | ttt | gga | aga | tac | aaa | aac | ttt | 480 |
| Asn | Ser | Lys | Gly | Glu | Tyr | Asn | Val | Pro | Phe | Gly | Arg | Tyr | Lys | Asn | Phe | |
| 145 | | | | | 150 | | | | | 155 | | | | | 160 | |
| aat | aca | aaa | atc | att | act | aaa | caa | cac | cat | aac | ctg | ctt | caa | aaa | aca | 528 |
| Asn | Thr | Lys | Ile | Ile | Thr | Lys | Gln | His | His | Asn | Leu | Leu | Gln | Lys | Thr | |
| | | | 165 | | | | | 170 | | | | | 175 | | | |
| gaa | ata | tat | aat | aaa | gat | ttt | tct | gaa | att | ttt | aag | atg | gca | aaa | cca | 576 |
| Glu | Ile | Tyr | Asn | Lys | Asp | Phe | Ser | Glu | Ile | Phe | Lys | Met | Ala | Lys | Pro | |
| | | | | 180 | | | | | 185 | | | | | 190 | | |
| aat | gac | ttc | atg | ttt | ctt | gat | cct | cca | tat | gat | tgt | att | ttt | agt | gat | 624 |
| Asn | Asp | Phe | Met | Phe | Leu | Asp | Pro | Pro | Tyr | Asp | Cys | Ile | Phe | Ser | Asp | |
| | | | 195 | | | | | 200 | | | | | 205 | | | |
| tat | gga | aat | atg | gag | ttt | aca | ggt | gat | ttc | gac | gag | agg | gaa | cat | cgt | 672 |
| Tyr | Gly | Asn | Met | Glu | Phe | Thr | Gly | Asp | Phe | Asp | Glu | Arg | Glu | His | Arg | |
| | 210 | | | | | 215 | | | | | 220 | | | | | |
| agg | ctt | gct | gaa | gag | ttt | aaa | aac | tta | aag | tgc | cgt | gca | cta | atg | atc | 720 |
| Arg | Leu | Ala | Glu | Glu | Phe | Lys | Asn | Leu | Lys | Cys | Arg | Ala | Leu | Met | Ile | |
| 225 | | | | | 230 | | | | | 235 | | | | | 240 | |
| att | agt | aaa | acg | gaa | tta | act | acc | gaa | cta | tat | aaa | gat | tat | atc | gtt | 768 |
| Ile | Ser | Lys | Thr | Glu | Leu | Thr | Thr | Glu | Leu | Tyr | Lys | Asp | Tyr | Ile | Val | |
| | | | | 245 | | | | | 250 | | | | | 255 | | |
| gat | gaa | tat | cat | aaa | agc | tat | tct | gta | aac | att | aga | aat | aga | ttt | aag | 816 |
| Asp | Glu | Tyr | His | Lys | Ser | Tyr | Ser | Val | Asn | Ile | Arg | Asn | Arg | Phe | Lys | |
| | | | 260 | | | | | 265 | | | | | 270 | | | |
| aat | gaa | gca | aag | cat | tat | ata | atc | aag | aac | tat | gat | tat | gta | cga | aaa | 864 |

```
Asn Glu Ala Lys His Tyr Ile Ile Lys Asn Tyr Asp Tyr Val Arg Lys
            275                 280                 285 aat aaa gaa gaa aaa tat gag caa ctt gaa ctt att cat tag              906
Asn Lys Glu Glu Lys Tyr Glu Gln Leu Glu Leu Ile His
        290                 295                 300
```

<210> SEQ ID NO 5
<211> LENGTH: 301
<212> TYPE: PRT
<213> ORGANISM: Bacillus stearothermophilus

<400> SEQUENCE: 5

```
Met Lys Pro Ile Leu Lys Tyr Arg Gly Gly Lys Lys Ala Glu Ile Pro
  1               5                  10                  15

Phe Phe Ile Asp His Ile Pro Asn Asp Ile Glu Thr Tyr Phe Glu Pro
                 20                  25                  30

Phe Val Gly Gly Gly Ala Val Phe Phe His Leu Glu His Glu Lys Ser
             35                  40                  45

Val Ile Asn Asp Ile Asn Ser Lys Leu Tyr Lys Phe Tyr Leu Gln Leu
         50                  55                  60

Lys His Asn Phe Asp Glu Val Thr Lys Gln Leu Asn Glu Leu Gln Glu
 65                  70                  75                  80

Ile Tyr Glu Lys Asn Gln Lys Glu Tyr Glu Lys Lys Ala Leu Ala
                 85                  90                  95

Pro Ala Gly Val Arg Val Glu Asn Lys Asn Glu Glu Leu Tyr Tyr Glu
            100                 105                 110

Leu Arg Asn Glu Phe Asn Tyr Pro Ser Gly Lys Trp Leu Asp Ala Val
        115                 120                 125

Ile Tyr Tyr Phe Ile Asn Lys Thr Ala Tyr Ser Gly Met Ile Arg Tyr
130                 135                 140

Asn Ser Lys Gly Glu Tyr Asn Val Pro Phe Gly Arg Tyr Lys Asn Phe
145                 150                 155                 160

Asn Thr Lys Ile Ile Thr Lys Gln His His Asn Leu Leu Gln Lys Thr
                165                 170                 175

Glu Ile Tyr Asn Lys Asp Phe Ser Glu Ile Phe Lys Met Ala Lys Pro
            180                 185                 190

Asn Asp Phe Met Phe Leu Asp Pro Pro Tyr Asp Cys Ile Phe Ser Asp
        195                 200                 205

Tyr Gly Asn Met Glu Phe Thr Gly Asp Phe Asp Glu Arg Glu His Arg
210                 215                 220

Arg Leu Ala Glu Glu Phe Lys Asn Leu Lys Cys Arg Ala Leu Met Ile
225                 230                 235                 240

Ile Ser Lys Thr Glu Leu Thr Thr Glu Leu Tyr Lys Asp Tyr Ile Val
                245                 250                 255

Asp Glu Tyr His Lys Ser Tyr Ser Val Asn Ile Arg Asn Arg Phe Lys
            260                 265                 270

Asn Glu Ala Lys His Tyr Ile Ile Lys Asn Tyr Asp Tyr Val Arg Lys
        275                 280                 285

Asn Lys Glu Glu Lys Tyr Glu Gln Leu Glu Leu Ile His
    290                 295                 300
```

<210> SEQ ID NO 6
<211> LENGTH: 852
<212> TYPE: DNA
<213> ORGANISM: Pseudomonas lemoignei
<220> FEATURE:
<221> NAME/KEY: CDS

<222> LOCATION: (1)..(849)

<400> SEQUENCE: 6

```
atg aag cca tta gtt aaa tat aga ggt gga aag tct aag gaa att cca      48
Met Lys Pro Leu Val Lys Tyr Arg Gly Gly Lys Ser Lys Glu Ile Pro
 1               5                  10                  15 tat cta att aaa cat atc cct gaa ttt aaa ggg cgc tac ata gag cct      96
Tyr Leu Ile Lys His Ile Pro Glu Phe Lys Gly Arg Tyr Ile Glu Pro
             20                  25                  30 ttt ttt ggt ggg ggg gct tta ttt ttt tat ata gag cca gaa aaa tct    144
Phe Phe Gly Gly Gly Ala Leu Phe Phe Tyr Ile Glu Pro Glu Lys Ser
         35                  40                  45 att atc aat gac att aat aaa aaa ctt ata gat ttt tat cga gat gtt    192
Ile Ile Asn Asp Ile Asn Lys Lys Leu Ile Asp Phe Tyr Arg Asp Val
 50                  55                  60 aaa gat aac ttt gtt caa ttg cgt cat gag ctt gat gag ata gaa tgt    240
Lys Asp Asn Phe Val Gln Leu Arg His Glu Leu Asp Glu Ile Glu Cys
 65                  70                  75                  80 att tat gaa aag aat aga gtt gaa tac gaa act aga aag aaa tta aat    288
Ile Tyr Glu Lys Asn Arg Val Glu Tyr Glu Thr Arg Lys Lys Leu Asn
                 85                  90                  95 cct act gaa cgt gta gat gat gga aat gaa gat ttc tat tac ttc atg    336
Pro Thr Glu Arg Val Asp Asp Gly Asn Glu Asp Phe Tyr Tyr Phe Met
            100                 105                 110 agg aat gaa ttc aat aaa gat ttt tcg gat aga tat ctt tca tca aca    384
Arg Asn Glu Phe Asn Lys Asp Phe Ser Asp Arg Tyr Leu Ser Ser Thr
        115                 120                 125 ctg tat ttt tat ata aat aag act gcg tac tct gga atg att aga tat    432
Leu Tyr Phe Tyr Ile Asn Lys Thr Ala Tyr Ser Gly Met Ile Arg Tyr
    130                 135                 140 aac tca aaa ggt gag ttt aat gtt ccg ttt ggt aga tat aaa aat ctc    480
Asn Ser Lys Gly Glu Phe Asn Val Pro Phe Gly Arg Tyr Lys Asn Leu
145                 150                 155                 160 aat aca aaa ctt gtg gct aat gaa cat cac ttg tta atg cag ggt gct    528
Asn Thr Lys Leu Val Ala Asn Glu His His Leu Leu Met Gln Gly Ala
                165                 170                 175 cag ata ttt aat gaa gat tac agc gag atc ttc aag atg gcg aga aaa    576
Gln Ile Phe Asn Glu Asp Tyr Ser Glu Ile Phe Lys Met Ala Arg Lys
            180                 185                 190 gat gat ttt ata ttt cta gac cct ccc tat gat tgc gta ttt agt gat    624
Asp Asp Phe Ile Phe Leu Asp Pro Pro Tyr Asp Cys Val Phe Ser Asp
        195                 200                 205 tat ggt aat gag gaa tat aaa gat ggt ttc aat gta gat gct cat gtg    672
Tyr Gly Asn Glu Glu Tyr Lys Asp Gly Phe Asn Val Asp Ala His Val
    210                 215                 220 aaa ttg agt gag gac ttt aag aaa ttg aaa tgc aaa gcc atg atg gtt    720
Lys Leu Ser Glu Asp Phe Lys Lys Leu Lys Cys Lys Ala Met Met Val
225                 230                 235                 240 atc ggt aag act gaa ttg act gat ggg ttg tat aag aaa atg att att    768
Ile Gly Lys Thr Glu Leu Thr Asp Gly Leu Tyr Lys Lys Met Ile Ile
                245                 250                 255 gat gaa tac gat aaa agt tat tct gtg aat ata agg aat aga ttt aag    816
Asp Glu Tyr Asp Lys Ser Tyr Ser Val Asn Ile Arg Asn Arg Phe Lys
            260                 265                 270 tct gtt gca aag cat ata gtt gtt gca aat tat tga                    852
Ser Val Ala Lys His Ile Val Val Ala Asn Tyr
        275                 280
```

<210> SEQ ID NO 7
<211> LENGTH: 283

```
<212> TYPE: PRT
<213> ORGANISM: Pseudomonas lemoignei

<400> SEQUENCE: 7

Met Lys Pro Leu Val Lys Tyr Arg Gly Gly Lys Ser Lys Glu Ile Pro
  1               5                  10                  15

Tyr Leu Ile Lys His Ile Pro Glu Phe Lys Gly Arg Tyr Ile Glu Pro
                 20                  25                  30

Phe Phe Gly Gly Gly Ala Leu Phe Phe Tyr Ile Glu Pro Glu Lys Ser
             35                  40                  45

Ile Ile Asn Asp Ile Asn Lys Lys Leu Ile Asp Phe Tyr Arg Asp Val
         50                  55                  60

Lys Asp Asn Phe Val Gln Leu Arg His Glu Leu Asp Glu Ile Glu Cys
 65                  70                  75                  80

Ile Tyr Glu Lys Asn Arg Val Glu Tyr Glu Thr Arg Lys Lys Leu Asn
                 85                  90                  95

Pro Thr Glu Arg Val Asp Asp Gly Asn Glu Asp Phe Tyr Tyr Phe Met
                100                 105                 110

Arg Asn Glu Phe Asn Lys Asp Phe Ser Asp Arg Tyr Leu Ser Ser Thr
            115                 120                 125

Leu Tyr Phe Tyr Ile Asn Lys Thr Ala Tyr Ser Gly Met Ile Arg Tyr
        130                 135                 140

Asn Ser Lys Gly Glu Phe Asn Val Pro Phe Gly Arg Tyr Lys Asn Leu
145                 150                 155                 160

Asn Thr Lys Leu Val Ala Asn Glu His His Leu Leu Met Gln Gly Ala
                165                 170                 175

Gln Ile Phe Asn Glu Asp Tyr Ser Glu Ile Phe Lys Met Ala Arg Lys
            180                 185                 190

Asp Asp Phe Ile Phe Leu Asp Pro Pro Tyr Asp Cys Val Phe Ser Asp
        195                 200                 205

Tyr Gly Asn Glu Glu Tyr Lys Asp Gly Phe Asn Val Asp Ala His Val
    210                 215                 220

Lys Leu Ser Glu Asp Phe Lys Lys Leu Cys Lys Ala Met Met Val
225                 230                 235                 240

Ile Gly Lys Thr Glu Leu Thr Asp Gly Leu Tyr Lys Lys Met Ile Ile
                245                 250                 255

Asp Glu Tyr Asp Lys Ser Tyr Ser Val Asn Ile Arg Asn Arg Phe Lys
            260                 265                 270

Ser Val Ala Lys His Ile Val Val Ala Asn Tyr
        275                 280

<210> SEQ ID NO 8
<211> LENGTH: 60
<212> TYPE: DNA
<213> ORGANISM: Bacillus stearothermophilus

<400> SEQUENCE: 8
gtgaattcga gctcggtacc cggggatcct ctagagtcga cctgcaggca tgcaagcttg    60

<210> SEQ ID NO 9
<211> LENGTH: 59
<212> TYPE: DNA
<213> ORGANISM: Bacillus stearothermophilus

<400> SEQUENCE: 9
ggtcgcggat ccgaattcga gctccgtcga caagcttgcg gccgcactcg agcaccacc    59
```

```
<210> SEQ ID NO 10
<211> LENGTH: 31
<212> TYPE: PRT
<213> ORGANISM: Bacillus stearothermophilus

<400> SEQUENCE: 10

Met Ala Lys Lys Val Asn Trp Tyr Val Ser Cys Ser Pro Trp Ser Pro
 1               5                  10                  15

Glu Lys Ile Gln Pro Glu Leu Lys Val Leu Ala Asn Phe Glu Gly
            20                  25                  30

<210> SEQ ID NO 11
<211> LENGTH: 12
<212> TYPE: PRT
<213> ORGANISM: Bacillus stearothermophilus
<220> FEATURE:
<223> OTHER INFORMATION: At position 2, Xaa=any amino acid

<400> SEQUENCE: 11

Met Xaa Ile Pro Tyr Glu Asp Phe Ala Asp Leu Gly
 1               5                  10

<210> SEQ ID NO 12
<211> LENGTH: 8
<212> TYPE: PRT
<213> ORGANISM: Bacillus stearothermophilus

<400> SEQUENCE: 12

Met Ala Lys Lys Val Asn Trp Tyr
 1               5

<210> SEQ ID NO 13
<211> LENGTH: 6
<212> TYPE: PRT
<213> ORGANISM: Bacillus stearothermophilus

<400> SEQUENCE: 13

Tyr Glu Asp Phe Ala Asp
 1               5

<210> SEQ ID NO 14
<211> LENGTH: 22
<212> TYPE: DNA
<213> ORGANISM: Bacillus stearothermophilus
<220> FEATURE:
<223> OTHER INFORMATION: At position 5 and 14, N=G, A, C, or T(U)
<223> OTHER INFORMATION: At position 8 and 11, R=A or G
<223> OTHER INFORMATION: At position 17, Y=C or T(U)

<400> SEQUENCE: 14
tggcnaaraa rgtnaaytgg ta                                              22

<210> SEQ ID NO 15
<211> LENGTH: 17
<212> TYPE: DNA
<213> ORGANISM: Bacillus stearothermophilus
<220> FEATURE:
<223> OTHER INFORMATION: At position 3, N=G, A, C or T(U)
<223> OTHER INFORMATION: At position 6 and 9, R=A or G
<223> OTHER INFORMATION: At position 12, Y=C or T(U)
<223> OTHER INFORMATION: At position 15, R=A or G

<400> SEQUENCE: 15
tcngcraart cytcrta                                                    17
```

```
<210> SEQ ID NO 16
<211> LENGTH: 24
<212> TYPE: DNA
<213> ORGANISM: Bacillus stearothermophilus

<400> SEQUENCE: 16
ctcttcatca ataacgaagt tgtt                                              24

<210> SEQ ID NO 17
<211> LENGTH: 25
<212> TYPE: DNA
<213> ORGANISM: Bacillus stearothermophilus

<400> SEQUENCE: 17
ttacaaccag ttactcatgc cgcag                                             25

<210> SEQ ID NO 18
<211> LENGTH: 24
<212> TYPE: DNA
<213> ORGANISM: Bacillus stearothermophilus

<400> SEQUENCE: 18
gagtgtgaaa gaaaatatac tcaa                                              24

<210> SEQ ID NO 19
<211> LENGTH: 27
<212> TYPE: DNA
<213> ORGANISM: Bacillus stearothermophilus

<400> SEQUENCE: 19
tatagttgtt cgatataatg agaccat                                           27

<210> SEQ ID NO 20
<211> LENGTH: 51
<212> TYPE: DNA
<213> ORGANISM: Pseudomonas lemoignei

<400> SEQUENCE: 20
aaaactgcag ataaggaggt gatcgtatga agccattagt taaatataga g                51

<210> SEQ ID NO 21
<211> LENGTH: 33
<212> TYPE: DNA
<213> ORGANISM: Pseudomonas lemoignei

<400> SEQUENCE: 21
cgcggatcct caataatttg caacaactat atg                                    33

<210> SEQ ID NO 22
<211> LENGTH: 48
<212> TYPE: DNA
<213> ORGANISM: Bacillus stearothermophilus

<400> SEQUENCE: 22
cgcggatcct aaggaggtga tctaatggct aaaaagtta attggtat                     48

<210> SEQ ID NO 23
<211> LENGTH: 33
<212> TYPE: DNA
<213> ORGANISM: Bacillus stearothermophilus

<400> SEQUENCE: 23
cccaagcttt taaaacctta cctccttgtc aac                                    33
```

-continued

```
<210> SEQ ID NO 24
<211> LENGTH: 36
<212> TYPE: DNA
<213> ORGANISM: Escherichia coli

<400> SEQUENCE: 24
accgcatcga atgcgagtcg aggacgacgg ccagtg                            36

<210> SEQ ID NO 25
<211> LENGTH: 38
<212> TYPE: DNA
<213> ORGANISM: Escherichia coli

<400> SEQUENCE: 25
cgattccgca atgcgagtcg aggccatgat tacgccaa                          38

<210> SEQ ID NO 26
<211> LENGTH: 13
<212> TYPE: DNA
<213> ORGANISM: Escherichia coli

<400> SEQUENCE: 26
cagtcacgac gtt                                                     13

<210> SEQ ID NO 27
<211> LENGTH: 13
<212> TYPE: DNA
<213> ORGANISM: Escherichia coli

<400> SEQUENCE: 27
cacaggaaac agc                                                     13
```

CLONING AND PRODUCING THE N.BSTNBI NICKING ENDONUCLEASE

BACKGROUND OF THE INVENTION

The present invention relates to the recombinant DNA which encodes the N.BstNBI nicking endonuclease and modification methylase, and the production of N.BstNBI nicking endonuclease from the recombinant DNA. N.BstNBI nicking endonuclease is originally isolated from *Bacillus stearothermophilus*. It recognizes a simple asymmetric sequence, 5' GAGTC 3', and it cleaves only one DNA strand, 4 bases away from the 3'-end of its recognition site.

Restriction endonucleases are enzymes that recognize and cleave specific DNA sequences. Usually there is a corresponding DNA methyltransferase that methylates and therefore protects the endogenous host DNA from the digestion of a certain restriction endonuclease. Restriction endonucleases can be classified into three groups: type I, II, and III. More than 3000 restriction endonucleases with over two hundred different specificities have been isolated from bacteria (Roberts and Macelis, *Nucleic Acids Res.* 26:338–350 (1998)). Type II and type IIs restriction enzymes cleave DNA at a specific position, and therefore are useful in genetic engineering and molecular cloning.

Most restriction endonucleases catalyze double-stranded cleavage on DNA substrate via hydrolysis of two phosphodiester bonds on two DNA strands (Heitman, *Genetic Engineering* 15:57–107 (1993)). For example, type II enzymes, such as EcoRI and EcoRV, recognize palindromic sequences and cleave both strands symmetrically within the recognition sequence. Type IIs endonucleases recognize asymmetric DNA sequences and cleave both DNA strands outside of the recognition sequence.

There are some proteins in the literature which break only one DNA strand and therefore introduce a nick into the DNA molecule. Most of those proteins are involved in DNA replication, DNA repair, and other DNA-related metabolisms (Kornberg and Baker, DNA replication. 2nd edit. W. H. Freeman and Company, New York, (1992)). For example, gpII protein of bacteriophage fI recognizes and binds a very complicated sequence at the replication origin. It introduces a nick in the plus strand, which initiates rolling circle replication, and it is also involved in circularizing the plus strand to generate single-stranded circular phage DNA. (Geider et al., *J. Biol. Chem.* 257:6488–6493 (1982); Higashitani et al., *J. Mol. Biol.* 237:388–400 (1994)). Another example is the MutH protein, which is involved in DNA mismatch repair in *E. coli*. MutH binds at dam methylation site (GATC), where it forms a protein complex with nearby MutS which binds to a mismatch. The MutL protein facilitates this interaction and this triggers single-stranded cleavage by MutH at the 5' end of the unmethylated GATC site. The nick is then translated by an exonuclease to remove the mismatched nucleotide (Modrich, *J. Biol. Chem.* 264:6597–6600 (1989)).

The nicking enzymes mentioned above are not very useful in the laboratory for manipulating DNA due to the fact that they usually recognize long, complicated sequences and usually associate with other proteins to form protein complexes which are difficult to manufacture. Thus none of these nicking proteins are commercially available. Recently, we have found a nicking protein, N.BstNBI, from the thermophilic bacterium *Bacillus stearothermophilus*, which is an isoschizomer of N.BstSEI (Abdurashitov et al., *Mol. Biol.* (Mosk) 30:1261–1267 (1996)). Unlike gpII and MutH, N.BstNBI behaves like a restriction endonuclease. It recognizes a simple asymmetric sequence, 5' GAGTC 3', and it cleaves only one DNA strand, 4 bases away from the 3'-end of its recognition site (FIG. 1A).

Because N.BstNBI acts more like a restriction endonuclease, it should be useful in DNA engineering. For example, it can be used to generate a DNA substrate containing a nick at a specific position. N.BstNBI can also be used to generate DNA with gaps, long overhangs, or other structures. DNA templates containing a nick or gap are useful substrate for researchers in studying DNA replication, DNA repair and other DNA related subjects (Kornberg and Baker, DNA replication. 2nd edit. W. H. Freeman and Company, New York, (1992)). A potential application of the nicking endonuclease is its use in strand displacement amplification (SDA), which is an isothermal DNA amplification technology. SDA provides an alternative to polymerase chain reaction (PCR), and it can reach $10^6$-fold amplification in 30 minutes without thermo-cycling (Walker et al., *Proc. Natl. Acad. Sci. USA* 89:392–396 (1992)). SDA uses a restriction enzyme to nick the DNA and a DNA polymerase to extend the 3'-OH end of the nick and displace the downstream DNA strand (Walker et al., (1992)). The SDA assay provides a simple (no temperature cycling, only incubation at 60° C.) and very rapid (as short as 15 minutes) detection method and can be used to detect viral or bacterial DNA. SDA is being introduced as a diagnostic method to detect infectious agents, such as *Mycobacterium tuberculosis* and *Chlamydia trachomatis* (Walker and Linn, *Clin. Chem.* 42:1604–1608 (1996); Spears et al., *Anal. Biochem.* 247:130–137 (1997)).

For SDA to work, a nick has to be introduced into the DNA template by a restriction enzyme. Most restriction endonucleases make double-stranded cleavages. Therefore, modified α-thio deoxynucleotides (dNTPαS) have to be incorporated into the DNA, so that the endonuclease only cleaves the unmodified strand which is within the primer region (Walker et al., 1992). The a-thio deoxynucleotides are eight times more expensive than regular dNTPs (Pharmacia), and is not incorporated well by the Bst DNA polymerase as compared to regular deoxynucleotides (J. Aliotta, L. Higgins, and H. Kong, unpublished observation).

Alternatively, if a nicking endonuclease is used in SDA, it will introduce a nick into the DNA template naturally. Thus the dNTPαS is no longer needed for the SDA reaction when a nicking endonuclease is being used. This idea has been tested, and the result agreed with our speculation. The target DNA can be amplified in the presence of the nicking endonuclease N.BstNBI, dNTPs, and Bst DNA polymerase.

With the advent of genetic engineering technology, it is now possible to clone genes and to produce the proteins that they encode in greater quantities than are obtainable by conventional purification techniques. Type II restriction-modification systems are being cloned with increasing frequency. The first cloned systems used bacteriophage infection as a means of identifying or selecting restriction endonuclease clones (EcoRII: Kosykh et al., *Molec. Gen. Genet* 178:717–719 (1980); HhaII: Mann et al., Gene 3:97–112 (1978); PstI: Walder et al., *Proc. Nat. Acad. Sci.* 78:1503–1507 (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acids Res.* 12:3659–3676 (1984); PaeR7: Gingeras and Brooks, *Proc. Natl. Acad. Sci. USA* 80:402–406 (1983); Theriault and Roy, *Gene* 19:355–359 (1982); PvuII: Blumenthal et al., *J. Bacteriol.* 164:501–509 (1985)).

A further approach which is being used to clone a growing number of systems involves selection for an active methylase gene (refer to U.S. Pat. No. 5,200,333 and BsuRI: Kiss et al., *Nucl. Acids Res.* 13:6403–6421 (1985)). Since restriction and modification genes are often closely linked, both genes can often be cloned simultaneously. This selection does not always yield a complete restriction system however, but instead yields only the methylase gene (BspRI: Szomolanyi et al., *Gene* 10:219–225 (1980); BcnI: Janulaitis et al, *Gene* 20:197–204 (1982); BsuRI: Kiss and Baldauf, *Gene* 21:111–119 (1983); and MspI: Walder et al., *J. Biol. Chem.* 258:1235–1241 (1983)).

Another method for cloning methylase and endonuclease genes is based on a colorimetric assay for DNA damage (see U.S. Pat. No. 5,492,823). When screening for a methylase, the plasmid library is transformed into the host *E.coli* strain such as AP1-200. The expression of a methylase will induce the SOS response in an *E.coli* strain which is McrA+, McrBC+, or Mrr+. The AP1-200 strain is temperature sensitive for the Mcr and Mrr systems and includes a lac-Z gene fused to the damage inducible dinD locus of *E.coli*. The detection of recombinant plasmids encoding a methylase or endonuclease gene is based on induction at the restrictive temperature of the lacZ gene. Transformants encoding methylase genes are detected on LB agar plates containing X-gal as blue colonies. (Piekarowicz et al., *Nucleic Acids Res.* 19:1831–1835 (1991) and Piekarowicz et al., *J. Bacteriology* 173:150–155 (1991)). Likewise, the *E.coli* strain ER1992 contains a dinD1-Lac Z fusion but is lacking the methylation dependent restriction systems McrA, McrBC and Mrr. In this system (called the "endo-blue" method), the endonuclease gene can be detected in the absence of it's cognate methylase when the endonuclease damages the host cell DNA, inducing the SOS response. The SOS-induced cells form deep blue colonies on LB agar plates supplemented with X-gal. (Fomenkov et al., *Nucleic Acids Res.* 22:2399–2403 (1994))

Sometimes the straight-forward methylase selection method fails to yield a methylase (and/or endonuclease) clone due to various obstacles, See, e.g., Lunnen et al., *Gene* 74(1):25–32 (1988). One potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease (see U.S. Pat. No. 5,320, 957).

Another obstacle to cloning restriction-modification systems lies in the discovery that some strains of *E.coli* react adversely to cytosine or adenine modification; they possess systems that destroy DNA containing methylated cytosine (Raleigh and Wilson, *Proc. Natl. Acad. Sci. USA* 83:9070–9074 (1986)) or methylated adenine (Heitman and Model, *J. Bacteriology* 196:3243–3250 (1987); Raleigh et al., *Genetics* 122:279–296 (1989); Waite-Rees et al., *J. Bacteriology* 173:5207–5219 (1991)). Cytosine-specific or adenine-specific methylase genes cannot be cloned easily into these strains, either on their own, or together with their corresponding endonuclease genes. To avoid this problem it is necessary to use mutant strains of *E. coli* (McrA– and McrB– or Mrr–) in which these systems are defective.

An additional potential difficulty is that some restriction endonuclease and methylase genes may not express in *E. coli* due to differences in the transcription machinery of the source organism and *E. coli,* such as differences in promoter and ribosome binding sites. The methylase selection technique requires that the methylase express well enough in *E. coli* to fully protect at least some of the plasmids carrying the gene.

Because purified restriction endonucleases, and to a lesser extent modification methylases, are useful tools for characterizing genes in the laboratory, there is a commercial incentive to obtain bacterial strains through recombinant DNA techniques that synthesize these enzymes in abundance. Such strains would be useful because they would simplify the task of purification as well as provide the means for production in commercially useful amounts.

SUMMARY OF THE INVENTION

A unique combination of methods was used to directly clone the N.BstNBI endonuclease gene and express the gene in an *E. coli* strain premodified by PleI methylase. To clone the N.BstNBI endonuclease gene directly, both the N-terminal amino acid sequence and a stretch of internal amino acid sequence of highly purified native N.BstNBI restriction endonuclease were determined. Degenerate primers were designed based on the amino acid sequences and PCR techniques were used to amplify a segment of the DNA gene that encodes the N.BstNBI endonuclease protein. The PCR product was sequenced and the information was used to design primers for inverse PCR reactions. By chromosome walking via inverse PCR, the endonuclease open reading frame, n.bstNBIR, was deduced. Continuing with inverse PCR, an open reading frame was found adjacent to the endonuclease gene. Blast analysis suggested that this gene encoded an adenine methylase (n.bstNBIM).

The N.BstNBI endonuclease gene was cloned into a low copy-number T7 expression vector, pHKT7, and transformed into an *E. coli* host which had been premodified by a pHKUV5-PleI methylase clone. This recombinant *E. coli* strain (NEB#1239) produces about $4 \times 10^7$ units N.BstNBI endonuclease per gram cell.

The present invention also relates to a novel method of DNA amplification. The example of using nicking endonuclease N.BstNBI in non-thio strand displacement amplification is disclosed.

BRIEF DESCRIPTION OF THE DRAWINGS

FIG. 2 shows the DNA sequence of n.bstNBIR gene and its encoded amino acid sequence (SEQ ID NO:2 AND SEQ ID NO:3).

FIG. 3 shows the DNA sequence of n.bstNBIM gene and its encoded amino acid sequence (SEQ ID NO:4 and SEQ ID NO:5).

FIG. 4 shows the DNA sequence of pleIM gene and its encoded amino acid sequence (SEQ ID NO:6 and SEQ ID NO:7).

DETAILED DESCRIPTION OF THE INVENTION

The cloning of the N.BstNBI restriction endonuclease gene from Bacillus stearothermophilus 33M (NEB #928, New England Biolabs, Inc., Beverly, Mass.) proved to be challenging. A methylase selection strategy was tried and one methylase expression clone was isolated. However, the flanking ORFs did not encode the N.BstNBI nicking enzyme. This turned out to be an orphan methylase, i.e., a methylase not associated with the cognate endonuclease gene. The method by which the N.BstNBI nicking endonuclease was preferably cloned and expressed in E. coli is described herein:

1. Purification of the N.BstNBI restriction endonuclease to near homogeneity and N-terminal and internal amino acid sequence determination.

Nine chromatography columns were used to purify the N.BstNBI endonuclease protein. They included an XK 50/14 fast flow P-cell column, an HR 16/10 Source™ 15Q, five HR 16/10 Heparin-TSK-Guardgel columns, an HR 10/10 Source™ 15Q column and a Resource™ 15S. The purification yielded one protein band at approximately 72 kDa on an SDS-PAGE protein gel following Coomassie blue staining. The N-terminal 31 amino acid residues were determined by sequential degradation of the purified protein on an automated sequencer. To determine its internal protein sequence, a 6-kDa polypeptide fragment was obtained following cyanogen bromide digestion of the 72-kDa N.BstNBI protein. The first 13 amino acid residues of this 6-kDa were determined. This 13-amino acid sequence differs from the sequence of the N-terminal 31 amino acid residues, suggesting it was internal N.BstNBI protein sequence.

2. Amplification of a segment of the N.BstNBI endonuclease gene and subsequent cloning.

Degenerate primers were designed based on both the N-terminal and internal amino acid sequences. These primers were used to PCR amplify the 5' end of the endonuclease gene. PCR products were cloned into plasmid pCAB16 and sequenced. The approximately 1.4 kb PCR fragment was then identified by comparing the amino acid sequences deduced from the cloned DNA with the N-terminal amino acid sequence of the N.BstNBI endonuclease protein.

3. Chromosome walking via inverse PCR to isolate the N.BstNBI endonuclease and methylase gene.

Figures 1A, 1B:
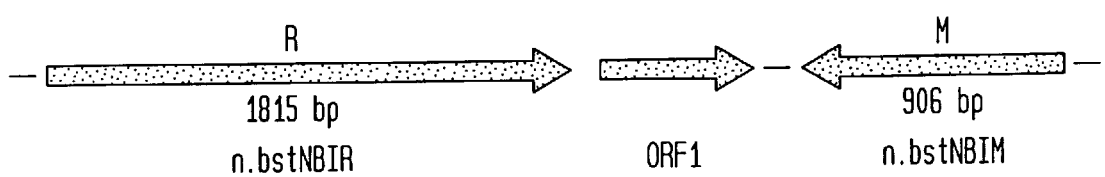
FIG. 1A shows the recognition sequence (SEQ ID No:1) and site of cleavage of N.BstNBI nicking endonuclease. N.BstNBI recognizes a simple asymmetric sequence, 5' GAGTC 3', and it cleaves only one DNA strand, 4 bases away from the 3'-end of its recognition site, indicated by the arrow head.
FIG. 1B shows the gene organization of N.BstNBI restriction modification system where n.bstNBIR (R) is the N.BstNBI restriction endonuclease gene and n.bstNBIM (M) is the N.BstNBI modification methyltransferase gene.

To clone the entire N.BstNBI endonuclease gene as well as its corresponding DNA methylase gene, inverse PCR techniques were adopted to amplify DNA adjacent to the original 1.4 kb endonuclease gene fragment (Ochman et al., Genetics 120:621 (1988); Triglia et al., Nucl. Acids Res. 16:8186 (1988) and Silver and Keerikatte, J. Cell. Biochem. (Suppl.) 13E:306, Abstract No. WH239 (1989)). In total, two rounds of inverse PCR were performed. At that point, the endonuclease and the methylase open reading frames (ORF) were identified (FIG. 1B).

The endonuclease gene (n.bstNBIR) turned out to be a 1815-bp ORF that codes for a 604-amino acid protein with a deduced molecular weight of 70,368 Daltons (FIG. 2). This agreed with the observed molecular mass of the N.Bst-NBI endonuclease that was purified from native Bacillus Stearothermophilus 33M. Close to the endonuclease gene a 906-bp ORF, n.bstNBIM, was found. It was oriented in a convergent manner relative to the endonuclease (FIG. 1B). The protein sequence deduced from n.bstNBIM gene shares significant sequence similarity with other adenine methylases (FIG. 3).

4. Expression of N.BstNBI endonuclease gene using pHKUV5 and pHKT7 plasmids.

The two-step method for cloning restriction-modification systems is described in U.S. Pat. No. 5,320,957. The first step is protection of the host cell from corresponding endonuclease digestion by pre-modification of recognition sequences. This is accomplished by introducing the methylase gene into a host cell and expressing the gene therein. The second step includes introduction of the endonuclease gene into the pre-modified host cell and subsequent endonuclease production.

The pleIM gene (FIG. 4) was cloned into plasmid pHKUV5 (FIG. 5) and transformed into E. coli cells. As a result, the E. coli cells were modified by the pHKUV5-pleIM. In this case, the PleI methylase (pleIM) was used for pre-modification of the host cells because PleI and N.Bst-NBI share the same recognition sequence.

Figure 6:
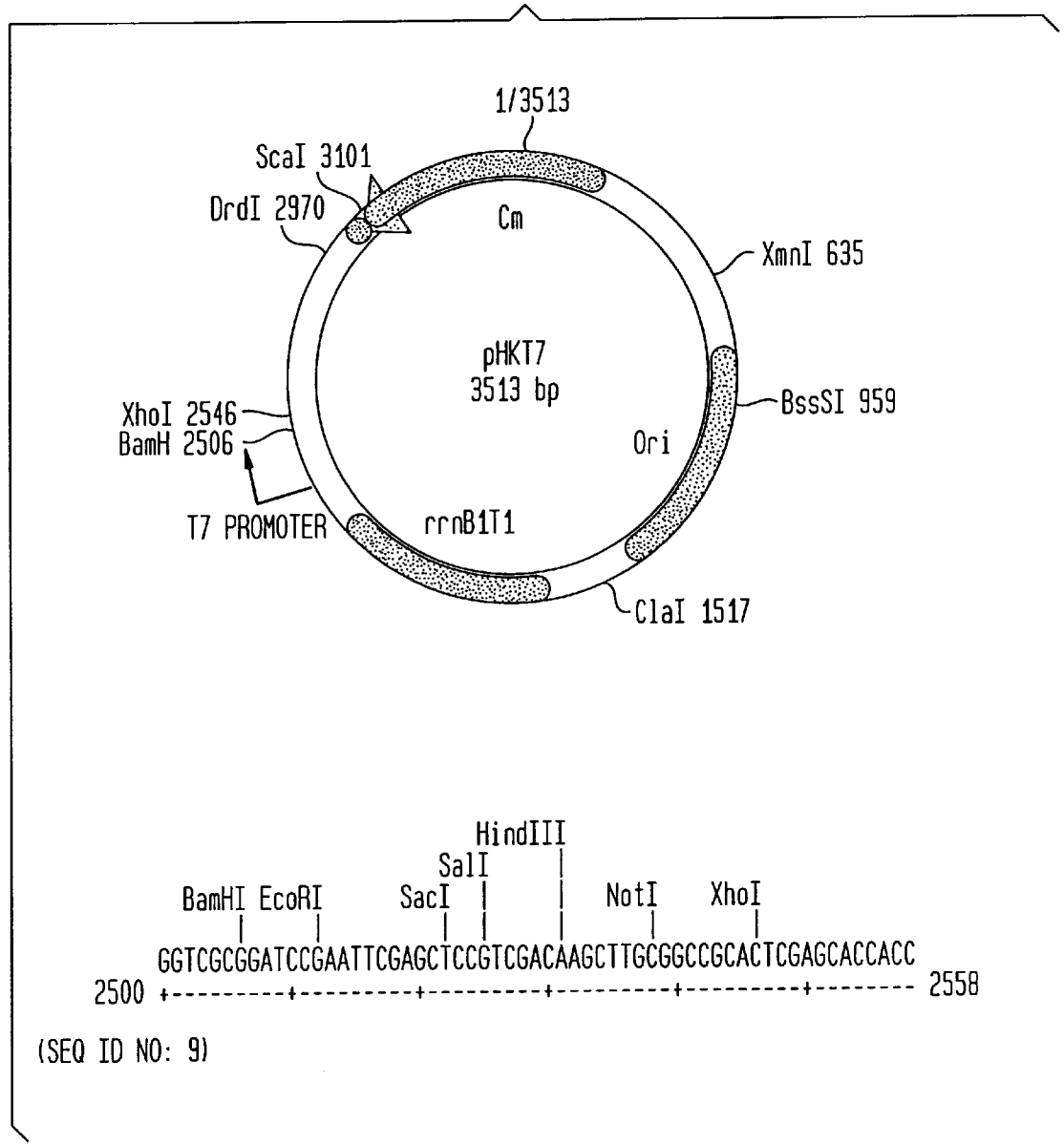
FIG. 6 shows the cloning vectors of pHKT7 (SEQ ID NO:9).

The endonuclease gene, n.bstNBIR, was cloned into pHKT7 (FIG. 6), and then introduced into E. coli ER2566 containing pHKUV5-pleIM. The culture was grown to middle log and then induced by the addition of IPTG to a final concentration of 0.4 mM. The yield of recombinant N.BstNBI endonuclease is $4 \times 10^7$ units per gram cells.

The following Examples are given to additionally illustrate embodiments of the present invention as it is presently preferred to practice. It will be understood that this Example is illustrative, and that the invention is not to be considered as restricted thereto except as indicated in the appended claims. The references cited above and below are incorporated by reference herein.

EXAMPLE 1

Purification of the N.BstNBI Endonuclease and Determination of its Protein Sequence 1. Purification of the N.BstNBI restriction endonuclease from Bacillus stearothermophilus 33M to near homogeneity:

Bacillus stearothermophilus 33M cells were propagated at 45° C. The cells were harvested by centrifugation after 20 hours of growth and stored at −70° C. until used. 177 g of cells were thawed at 4° C. overnight and then resuspended in 530 ml of Buffer A (20 mM $KPO_4$, 7 mM BME, 0.1 mM EDTA, 5% glycerol, pH 6.9) supplemented with 100 mM NaCl. The cells were broken with a Manton-Gaulin homogenizer. 25 ml of protease inhibitor cocktail (P8465; Sigma, St. Louis, Mo.) was added after the first pass. The extract was centrifuged at 14,000 rpm for 10 minutes at 4° C.

All of the following procedures were performed on ice or at 4° C. The supernatant was loaded onto a 275 ml XK 50/14 fast flow Phosphocellulose column (Whatman International Ltd., Kent, England) equilibrated with Buffer A.1 (100 mM NaCl, 20 mM $KPO_4$, 0.1 mM EDTA, 7 mM beta-mercaptoethanol and 5% glycerol, pH 6.9). The column was washed with 2× volume of Buffer A.1, followed by a 10× linear gradient from 100 mM NaCl to 1 M NaCl in Buffer A (20 mM KPO$_4$, 0.1 mM EDTA, 7 mM beta-mercaptoethanol and 5% glycerol, pH 6.9). 25 ml fractions were collected. Fractions were assayed for N.BstNBI restriction activity with T7 DNA at 55° C. in 1× N.BstNBI Buffer (150 mM KCl, 10 mM Tris-HCl, 10 mM MgCl$_2$, 1 mM dithiothreitol, 100 μg/ml BSA, pH 8.0). The peak of restriction enzyme activity was found to elute from the column at approximately 200 mM NaCl.

The active fractions, 39–57, were pooled (475 ml) and dialyzed against 100 mM NaCl supplemented Buffer B (20 mM Tris-HCl, 0.1 mM EDTA, 7 mM beta-mercaptoethanol and 5% glycerol, pH 8.0). The dialyzed pool was then diluted with Buffer B to a final concentration of 50 mM NaCl. There was a cloudy precipitate that formed but this was spun out by centrifugation in a large rotor at 14,000 rpm for 30 minutes. The cleared solution was then applied to a 22 ml HR 16/10 Sourcem 15Q column (Pharmacia Biotech, Piscataway, N.J.) equilibrated in Buffer B.1 (50 mM NaCl, 20 mM Tris-HCl, 0.1 mM EDTA, 7 mM beta-mercaptoethanol and 5% glycerol, pH 8.0). The column was washed with 2× volume of buffer B1 followed by a 10× linear gradient from 50 mM NaCl to 800 mM NaCl in Buffer B. 10 ml fractions were collected. Fractions were assayed for N.BstNBI activity as above. The majority of the restriction enzyme activity flowed through the column. However, fractions 6–10, which eluted at approximately 110 mM NaCl, had quite a bit of activity and were pooled (50 ml) and diluted to 50 mM NaCl in Buffer B. They were later loaded onto the second Heparin column.

The Source Q flow through and wash were combined and loaded onto a 23 ml HR 16/10 Heparin TSK-guard gel 5PW (20 μm) column (TosoHaas, Montgomeryville, Pa.) that had been equilibrated with Buffer B.2 (Buffer B with 100 M NaCl). The column was washed with 2× volume of Buffer B.2 and then a 10× linear gradient from 100 mM NaCl to 1 M NaCl in Buffer B was performed. 7 ml fractions were collected. Fractions were assayed for N.BstNBI activity as above. Activity was found in the fractions that were eluted at approximately 550 mM NaCl. Fractions 36–39 were pooled (28 ml) and diluted to 50 mM NaCl with Buffer B.

A second HR 16/10 Heparin TSK-guard gel was then run but with diluted fractions 6–10 off of the Source Q. All conditions were the same as the first Heparin column with the only exception being that a 20× gradient was run instead of a 10× gradient. Activity was found in the fractions that were eluted at approximately 550 mM NaCl. Fractions 36–38 were pooled (21 ml) and diluted to 50 mM NaCl with Buffer B.

This pool was then combined with the pooled and diluted fractions off of the first Heparin column and loaded onto an 8 ml HR 10/10 Source™ 15Q column that had been equilibrated with Buffer B.1. The column was washed with 2× volume of Buffer B.1 and then a 15× linear gradient from 50 mM NaCl to 800 mM NaCl in Buffer B was performed. Three ml fractions were collected. Fractions were assayed for N.BstNBI activity as above. The majority of the activity flowed through. However, some activity was detected in the first 14 fractions. The flow through and wash were pooled and then fractions 1–14 were pooled (42 ml) separately from the flow through and wash. The 1–14 pool was diluted to 50 mM NaCl in Buffer B. The flow through and wash pool was run over a third Heparin column (same type as above). A 20× gradient was run from 50 mM to 1 M NaCl in Buffer B. Four ml fractions were collected. N.BstNBI was eluted at approximately 590 mM NaCl. Fractions 24–26 were pooled (12 ml) and diluted to 50 mM NaCl in Buffer A.

At the same time, pooled and diluted fractions 1–14 off of the HR 10/10 Source™ 15Q were loaded onto a fourth Heparin column (same type as above). A 20× gradient was run from 50 mM to 1 M NaCl in Buffer B. 4 ml fractions were collected. N.BstNBI was eluted at approximately 590 mM NaCl. Fractions 24–26 were pooled (12 ml) and diluted to 50 mM NaCl in Buffer A.

The pooled and diluted fractions off of the third and fourth Heparin columns were combined and run over a fifth Heparin column (same type as above). Note that this time, the Heparin column was run in a phosphate buffer as opposed to a Tris-HCl buffer. The diluted pool was loaded onto the HR 16,/10 Heparin TSK-guard gel column that had been previously equilibrated with Buffer A.2 (Buffer A plus 50 mM NaCl). The column was washed with a 2× volume of Buffer A.2 followed by a 20× linear gradient from 50 mM NaCl to 1 M NaCl in Buffer A. 3 ml fractions were collected. Fractions were assayed for N.BstNBI activity. The peak of the enzyme activity eluted at approximately 630 mM NaCl. Fractions 34 through 36 were pooled (9 ml) and diluted to 50 mM NaCl in Buffer A.

The diluted pool was loaded onto a 1 ml Resource™ 15S (Pharmacia Biotech, Piscataway, N.J.) prepacked column that had been previously equilibrated with Buffer A.2. The column was washed with a 2× volume of Buffer A.2 followed by a 20× linear gradient from 50 mM to 1 M NaCl in Buffer A. One ml fraction was collected. The majority of the activity was found in fractions 13–19 (7 ml) with the most activity being in fraction 15. The apparent salt for the elution was 750 mM NaCl; but, since the protein precipitated on the column, this isn't the "real" elution salt concentration.

The N.BstNBI was purified to approximately 80% homogeneity. Twenty μL of the peak fractions (13–18) were loaded onto an SDS-PAGE protein gel and subjected to electrophoresis. The gel was stained with Coomassie blue R-250 and a prominent band at approximately 72 kDa corresponding to the N.BstNBI restriction endonuclease activity was observed.

2. Determination of the N-terminal and internal protein sequence of N.BstNBI endonuclease The N.BstNBI restriction endonuclease, prepared as described, was subjected to electrophoresis and electroblotted according to the procedure of Matsudaira (Matsudaira, J. Biol. Chem. 262:10035–10038 (1987)), with modifications as previously described (Looney et al., Gene 80:193–208 (1989)). The membrane was stained with Coomassie blue R-250 and the protein bands of approximately 72 kDa and 6 kDa were excised and subjected to sequential degradation on an Applied BioSystems Division, Perkin-Elmer Corporation (Foster City, Calif.) Model 407A gas phase protein sequencer (Waite-Rees et al., J. Bacteriol. 173:5207–5219 (1991)). The first 31 residues of the 72 kDa protein band corresponded to M-A-K-K-V-N-W-Y-V-S-C-S-P-W-S-P-E-K-I-Q-P-E-L-K-V-L-A-N-F-E-G (SEQ ID NO:10) and the amino acid sequence from the N-termini of the 6 kDa internal piece of the protein was M-X-I-P-Y-E-D-F-A-D-L G (SEQ ID NO:11).

EXAMPLE 2

Cloning of the N.BstNBI Restriction-Modification Genes

1. Purification of genomic DNA from *Bacillus stearothermophilus* 33M

To prepare the genomic DNA of *Bacillus stearothermophilus* 33M, 6.7 g of cells were resuspended in 20 ml of 25% Sucrose, 50 mM Tris, pH 8.0 and mixed until the solution was homogenous. Ten ml of 0.25M EDTA (pH 8.0) plus 6 ml of freshly-prepared 10 mg/ml lysozyme in 0.25M Tris-HCl (pH 8.0) were added and the solution was incubated on ice for 2 hours. Twenty four ml of Lytic mix (1% Triton-X100, 50 mM Tris, 62 mM EDTA, pH 8.0) and 5 ml of 10% SDS were then added and the solution was gently mixed. The solution was extracted with one volume of equilibrated phenol/chloroform (50:50, v/v) and the aqueous phase was recovered. The aqueous solution was then dialyzed overnight at 4° C., against 4 L of 10 mM Tris-HCl (pH 8.0), 1 mM EDTA. The dialyzed solution was digested with RNase A (100 μg/ml) at 37° C. for 1 hour. The DNA was precipitated by the addition of 1/10th volume 5 M NaCl and 0.55 volume of 2-propanol and spooled on a glass rod. The remaining solution was spun at 12,000 RPM for 30 minutes and the supernatant was then discarded. Both the spooled DNA a nd the centrifuged DNA pellet were air dried and dissolved in a total of 3.5 ml TE (10 mM Tris, 1 mM EDTA, pH 8.0). The final concentration was approximately 100 μg/ml and the DNA was stored at 4° C.

2. Cloning the 5' region of the N.BstNBI endonuclease gene into pCAB16 pCAB16 was digested with BsaAI by incubating the vector for 1 hour at 37° C. in the conditions described below.

120 μl pCAB 16 (6–12 μg)

10 μl BsaAI (50U)

40 μl 10× NEB Buffer #3

230 μl dH$_2$O

The BsaAI in the reaction was heat killed by incubating for 15 minutes at 75° C. The vector was then dephosphorylated by incubating 100 μl (2 μg) of digested vector with 1 unit of shrimp alkaline phosphatase in 100 mM MgCl$_2$ for 1 hour at 37° C.

Degenerate primers were designed based on the following amino acid sequences derived from the N.BstNBI N-terminal protein sequence and internal protein sequence respectively: 1) M-A-K-K-V-N-W-Y (SEQ ID NO:12) and 2) Y-E-D-F-A-D (SEQ ID NO:13). They were designed to hybridize in a convergent manner with DNA at the 5' end of the N.BstNBI endonuclease gene.

Primer 1 5' TGGCNAARAARGTNAAYTGGTA 3' (SEQ ID NO:14)

Primer 2 5' TCNGCRAARTCYTCRTA 3' (SEQ ID NO:15)

These primers were synthesized and each was kinased by incubating 2 μg of primer with 20 units of T4 Polynucleotide Kinase, 4 μl 10× T4 Polynucleotide Kinase Buffer, and 4 μl of 10 mM ATP, in a 40 μl reaction volume at 37° C. for 30 minutes. The kinase was heat inactivated by incubating the reaction at 65° C. for 10 min.

In the reaction that was successful in amplifying the product, a reaction mix was made by combining:

10 μl of 10× NEB ThermoPol Buffer

10 μl of 2 mM dNTP solution 1.5 μl of kinased primer 1 (75 ng)

1.5 μl of kinased primer 2 (75 ng)

1 μl of purified bacterial DNA template (100 ng)

72 μl dH$_2$O

2 μl (4 units) of Vent®(exo-) DNA Polymerase

The PCR amplification conditions were: 32 cycles of 95° C. for 30 seconds, 45° C. for 1 minute and 72° C. for 1 minute. The reaction was electrophoresed on a 1% low melting temperature agarose gel (NuSieve Agarose, FMC BioProducts, Rockland, Me.) in TAE buffer (40 mM Tris-Acetate, pH 8, 1 mM EDTA). An approximately 1.4 Kb DNA band was excised and the gel slice was frozen overnight. The agarose plug was digested with Beta-Agarase by the addition of 2 μl of Beta-Agarase (2 units) and an incubation of 40° C. for one hour. The reaction was frozen and then thawed and microcentrifuged briefly to remove any undigested agarose pieces. The remaining aqueous layer was ethanol precipitated and the final purified DNA pellet was resuspended to 5 ng/μl. A ligation was then performed by combining the following at 37° C.:

1 μl prepared pCAB16 (50 ng)

20.5 μl PCR product (100 ng)

2.5 μl 10× T4 DNA Ligase Buffer

1 μl concentrated T4 DNA Ligase (2000 units)

The reaction was incubated at 37° C. for one hour and then it was placed in the refrigerator in an ice bucket filled with water and ice. The reaction was incubated as such overnight. Ten μl of the overnight ligation reaction was transformed into 100 μl of competent ER2502 cells by combining the DNA and cells and incubating on ice for 10 minutes followed by 45 seconds at 42° C. The entire volume was plated on an Ampicillin LB plate and incubated overnight at 37° C. Colonies that grew were inspected for the correct plasmid construct by purifying the plasmid DNA using the Quiagen QIAprep Spin Plasmid Kit and digesting with AseI to see if the PCR product was cloned into the vector.

4 μl miniprep 1.5 μl 10× X NEB #3

0.5 μl AseI

9 μl dH$_2$O

The above reaction was incubated at 37° C. for one hour. Minipreps containing the correct size insert were sequenced. The DNA sequence was translated in six reading frames to check whether the deduced amino acid sequence corresponded with the N-terminal sequence of N.BstNBI protein.

3. Chromosome walking via inverse PCR to isolate the N.BstNBI endonuclease and methylase genes A) Genomic DNA preparation—Two templates were prepared for two consecutive inverse PCR reactions; HincII and SspI. In the case of HincII, 1.5 μg of bacterial DNA was digested with 50 units of HincII restriction endonuclease in 1× NEBuffer 3 supplemented with BSA to a final concentration of 0.1 mg/ml in a 50 μl reaction volume. In the case of SspI, 1.5 μg of bacterial DNA was digested with 25 units of SspI restriction endonuclease in 1× NEBuffer SspI in a 50 μl reaction volume. Both reactions were incubated at optimum temperatures for one hour. The digests were confirmed by running 13 μl of the digestion reaction on a 1% agarose gel. The remaining reactions were then heat killed by incubating at 65° C. for 20 minutes. Circularization was then achieved by incubating the remaining 37 μl (~1 μg) in 1× T4 DNA Ligase Buffer with 3000 units of T4 DNA Ligase in a 500 μl reaction volume at 16° C. overnight. A portion of this circularization ligation reaction was then used as the template for subsequent inverse PCR reactions.

B) HincII inverse PCR—Inverse PCR primers were synthesized based on the DNA sequence of the piece of N.BstNBI endonuclease gene cloned into pCAB16:

5'- CTCTTCATCAATAACGAAGTTGTT -3' (SEQ ID NO:16) (221-85)

5'- TTACAACCAGTTACTCATGCCGCAG -3' (SEQ ID NO:17) (221-86)

Inverse PCR was carried out using primers 221-85 and 221-86 and the above mentioned HincII DNA template. An approximately 650 base pair product was produced. This product was gel purified and resuspended in 30 μl dH$_2$O. The PCR product was then sequenced using an ABI 373 automated sequencing system according to the manufacturer's instructions. The PCR primers above were used as the sequencing primers. The HincII inverse PCR product contained approximately 410 novel bp of the N.BstNBI ORF.

C. SspI inverse PCR reaction—Two inverse PCR primers complementary to sequence read from the HincII inverse PCR product were synthesized (see below) and a second inverse PCR reaction was performed. Template preparation, inverse PCR, purification and DNA sequencing were all done the same as above with the exception that the SspI ligation was used to create the template as opposed to the HincII ligation. An approximately 2.2 Kb PCR product was generated and sequenced. The data revealed the remaining endonuclease ORF sequence and the n.bstNBIM DNA sequence.

5' GAGTGTGAAAGAAAATATACTCAA 3' (SEQ ID NO:18) (222-145)

5' TATAGTTGTTCGATATAATGAGACCAT 3' (SEQ ID NO:19) (222-146)

EXAMPLE 3

Expression of the N.BstNBI Restriction Endonuclease

1. Cloning the PleI methylase on a compatible vector

Figure 5:
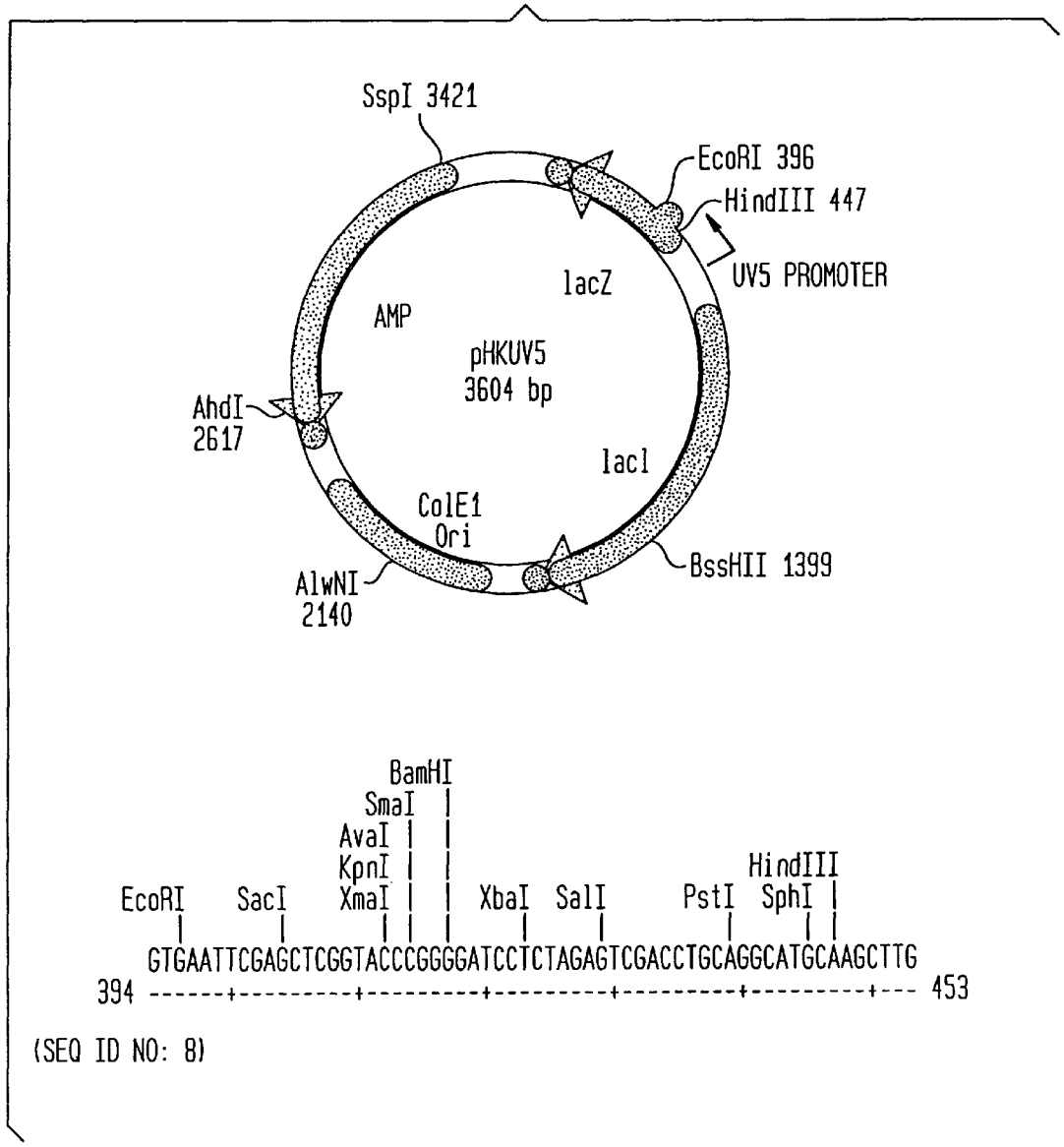
FIG. 5 shows the cloning vectors of pHKUV5 (SEQ ID NO:8).

The PleI methylase gene (pleIM) was expressed by inserting the gene into an expression vector, pHKUV5, directly downstream of the strong UV5 promoter (FIG. 5). To accomplish this, two oligonucleotide primers were synthesized utilizing the DNA sequence data. The forward oligonucleotide primer contained a PstI site to facilitate cloning, a stop codon in frame with the lacZ gene to terminate translation of the lacZ protein, a ribosome binding site (RBS) and 25 nucleotides complementary to *Pseudomonas lemoignei* DNA for hybridization:

5'-AAAACTGCAGATAAGGAGGTGATCGTATGAAG CCATTAGTTAAATATAGAG-3' (212-180) (SEQ ID NO:20)

The reverse primer was designed to hybridize to *Pseudomonas lemoignei* DNA at the 3' end of the PleI gene. It contained a BamHI restriction site to facilitate cloning.

5'-CGCGGATCCTCAATAATTTGCAACAACTATATG -3' (212-175) (SEQ ID NO:21)

These two primers were used to amplify the pleIM gene from genomic *Pseudomonas lemoignei* DNA by combining:

10 μl 10× Vent® ThermoPol Buffer
10 μl of 2 mM dNTPs
4 μl (300 ng) *Pseudomonas lemoignei* genomic DNA
1 μl primer 212-180 (75 ng)
1 μl primer 212-175 (75 ng)
72 μl dH$_2$O
1 μl (0.1 units) Deep Vent® polymerase
1 μl Taq DNA polymerase (5 units)

and amplifying for 25 cycles at 94° C. for 5 minutes, 50° C. for 1 minute and 72° C. for 2 minutes. The amplification product was purified using the Promega Wizard PCR Prep Kit. 500 ng of pHKUV5 vector and the remaining PCR product (~2 μg) were both digested with 20 units of BamHI and 20 units of PstI, supplemented with 0.1 mg/ml BSA in 1× NEB BamHI buffer in a 60 μl reaction that was incubated at 37° C. for one hour. The digests were run on a 1% low melting temperature NuSieve agarose gel in TAE buffer. The PCR and vector DNA bands were cut out of the gel. The plasmid gel slice was treated with Beta-Agarase for one hour at 40° C. It was then frozen and thawed and the remaining solid gel pieces were quickly spun out using a microcentrifuge. The supernatant was ethanol precipitated and the final DNA pellet was resuspended in water. The DNA concentration was determined by visual inspection on an agarose gel. The methylase PCR was not gel purified as the vector was. The gel plug containing the methylase PCR product was used directly in the ligation reaction. The ligation of pHKUV5 and pleIM was accomplished by combining the following:

5 μl prepared pHKUV5 (100 ng)
5 μl methylase PCR product (100 ng)
1 μl Beta-Agarase (1 unit)
5 μl 10× T4 DNA Ligase Buffer
1 μl concentrated T4 DNA Ligase (2000 units)
33 μl dH$_2$O The reaction was incubated at 37° C. for one hour and ten μl of the ligation reaction was transformed into *E. coli* strain ER2502. Individual colonies were isolated and analyzed by digesting minipreps with the cloning enzymes to ensure that the methylase gene had indeed been cloned into the vector:

3 μl miniprep
1.5 μl 10× BamHI buffer
1.5 μl 1 mg/ml BSA
0.75 μl PstI (15 U)
0.75 μl BamHI (15 U)
7.5 μl dH$_2$O The digests were incubated at 37° C. for one hour.

The minipreps that were the correct construct were then digested with PleI to check for methylase protection:

3 μl miniprep
1.5 μl 10× NEBuffer 1
1.5 μl 1 mg/ml BSA
1 μl PleI (1 unit)
8 μl dH$_2$O The digests were incubated at 37° C. for one hour. One μl of a clone that was resistant to PleI digestion was transformed into ER2566 cells for the purpose of making calcium chloride competent cells.

2. Cloning and expression of the N.BstNBI endonuclease gene

The N.BstNBI endonuclease gene (n.bstNBIR) was expressed by inserting the gene into an expression vector, pHKT7, directly downstream of a strong inducible T7 promoter and a conserved ribosome binding site (RBS). To accomplish this, two oligonucleotide primers were synthesized utilizing the DNA sequence data. The forward oligonucleotide primer contained a BamHI site to facilitate cloning, an ATG start codon of the N.BstNBI endonuclease gene and 24 nucleotides complementary to Bacillus stearothermophilus 33M DNA for hybridization:

5'- CGCGGATCCTAAGGAGGTGATCTAATG- GCTAAAAAAGTTAATTGGTAT -3' (223-138) (SEQ ID NO:22)

The reverse primer was designed to hybridize to *Bacillus stearothermophilus* 33M DNA at the 3' end of the n.bstNBIM gene. It contained a HindIII restriction site to facilitate cloning.

5'-
CCCAAGCTTTTAAAACCTTACCTCCTTGTCAAC-
3' (223-139) (SEQ ID NO:23)

These two primers were used to amplify the n.bstNBIM gene from *Bacillus stearothermophilus* 33M genomic DNA by combining:

15 µl 10× Taq PCR Buffer (containing 1.5 mM Mg++)
15 µl 2 mM dNTPs
3 µl (240 ng) *Bacillus stearothermophilus* 33M genomic DNA
1.5 µl primer 223-138 (112.5 ng)
1.5 µl primer 223-139 (112.5 ng)
111 µl dH$_2$O
1.5 µl (0.075 units) Deep Vent® polymerase
1.5 µl Taq DNA polymerase (7.5 units)

and amplifying for 25 cycles at 94° C. for 30 seconds, 50° C. for 1 minute and 72° C. for 2 minutes. The amplification product was purified using the Qiagen PCR Purification Kit. 1 µg of pHKT7 vector and the remaining PCR product (~2 µg) were both digested with 20 units of BamHI and 20 units of HindIII, supplemented with 0.1 mg/ml BSA in 1× NEB BamHI buffer. The reactions were incubated at 37° C. for one hour. The digests were run on a 1% low melting-point NuSieve agarose gel in TAE buffer. The PCR and vector DNA bands (approximately 1.8 Kb and 3.5 Kb respectively) were cut out and the gel slices were incubated at 65° C. for 10 minutes. The temperature was reduced to 37° C. and the gel slices were ligated. The ligation of pHKT7 and n.bstNBIM was performed by combining the following at 37° C.:

5 µl pHKT7 gel slice (50 ng)
5 µl endonuclease PCR product gel slice (100 ng)
2.5 µl 10× T4 DNA Ligase Buffer
1.5 µl T4 DNA Ligase (600 units)
1 µl Beta-Agarase (1 unit)
10 µl dH$_2$O The reaction was incubated at 37° C. for one hour and then at 25° C. for another hour. Ten µl of the ligation reaction was transformed into *E. coli* strain ER2566 previously modified with the PleI methylase gene. Transformants were analyzed and all contained the n.bstNBIM gene. This plasmid construct, pHKT7-n.bstNBIM, was selected for producing the N.BstNBI endonuclease. The *E. coli* strain which contains both pHKT7-n.bstNBIR and pHKUV5-pleIM plasmids was designated as NEB#1239. The yield of recombinant N.BstNBI from strain NEB#1239 was approximately 4×10$^7$ units/gram of cells.

3. Producing the recombinant N.BstNBI restriction endonuclease from *E. coli* ER2566 NEB#1239

*E. coli* ER2566 NEB#1239 was grown to mid-log phase in a fermenter containing L-broth medium with ampicillin (100 µg/ml) and chloramphenicol (50 µg/ml). The culture was induced by the addition of IPTG to a final concentration of 0.4 mM and allowed to continue growing for 16 hours. The cells were harvested by centrifugation and were stored at −70° C.

Purification of the N.BstNBI restriction endonuclease from *E. coli* NEB#1239 can be accomplished by a combination of standard protein purification techniques, such as affinity-chromatography or ion-exchange chromatography, as outlined in Example 1 above. The N.BstNBI restriction endonuclease obtained from this purification is substantially pure and free of non-specific endonuclease and exonuclease contamination.

A sample of the *E. coli* ER2566 NEB#1239 which contains both pHKUV5-pleIM and pHKT7-n.bstNBIR plasmids has been deposited under the terms and conditions of the Budapest Treaty with the American Type Culture Collection on May 26, 2000 and received ATCC Accession No. PTA-1925. The address of the ATCC is 10801 University Blvd. Manassas, Va. 20110-2209.

EXAMPLE 4

Non-thio Strand Displacement Amplification Using N.BstNBI

For strand displacement amplification (SDA) to work, a nick has to be introduced into the DNA template by a restriction enzyme.

Most restriction endonucleases make double stranded breaks and therefore, a-thio dNTPs have to be used in SDA. We have tested the nicking endonuclease N.BstNBI in non-thio SDA and we found the target DNA could be successfully amplified. The following is the detailed protocol for non-thio SDA with N.BstNBI.

1. Prepare mix A (below) in a plastic 1.5 ml tube at 4° C.:

| Reagent Stock | Final Concentration | 40 µl Volume |
|---|---|---|
| 250 mM KPO4, (pH 7.5) | 35 mM KPO4 | 7 µl |
| 2 M kCl | 100 mM | 2.5 µl |
| 4 mM each dNTP mix | 200 mM each dNTP | 2.5 µl |
| 100 mM DTT | 1 mM | 0.5 µl |
| 10 µM Primer 40 | 0.8 µM | 4 µl |
| 10 µM Primer 41 | 0.8 µM | 4 µl |
| 2.5 µM bump Primer 1 | 0.05 µM | 1 µl |
| 2.5 µM bump Primer 2 | 0.05 µM | 1 µl |
| 50 ng/µl DNA template | 1 ng/µl | 1 µl |
| H$_2$O | | 16.5 µl |

2. Denature at 100° C. for 2 minutes; incubate at 55° C. for 3 minutes to allow annealing of the primers. While these two temperature incubations are occurring, prepare mix B (below) in a separate plastic 1.5 ml tube and preincubate at 55° C. for at least 30 seconds.

| Reagent Stock | Final Concentration | 10 µl Volume |
|---|---|---|
| 10X NEBuffer 2 | 1 X | 5.0 µl |
| 10 mg/ml purified BSA | 100 µg/ml | 0.5 µl |
| 50 mM MgCl$_2$ | 2.5 mM MgCl2 | 2.5 µl |
| 10 units/µl N.BstNBI | 5 units per 50 µl | 0.5 µl |
| 20 units/µl Bst DNA Pol | 10 units per 50 µl | 0.5 µl |
| H$_2$O | | 1 µl |

3. Add mix A to B; continue incubation at 55° C. for 20–60 minutes, removing 10–20 µl volumes at different time points if desired; add to stop dye containing 0.2% SDS (final concentration).

Figure 7:
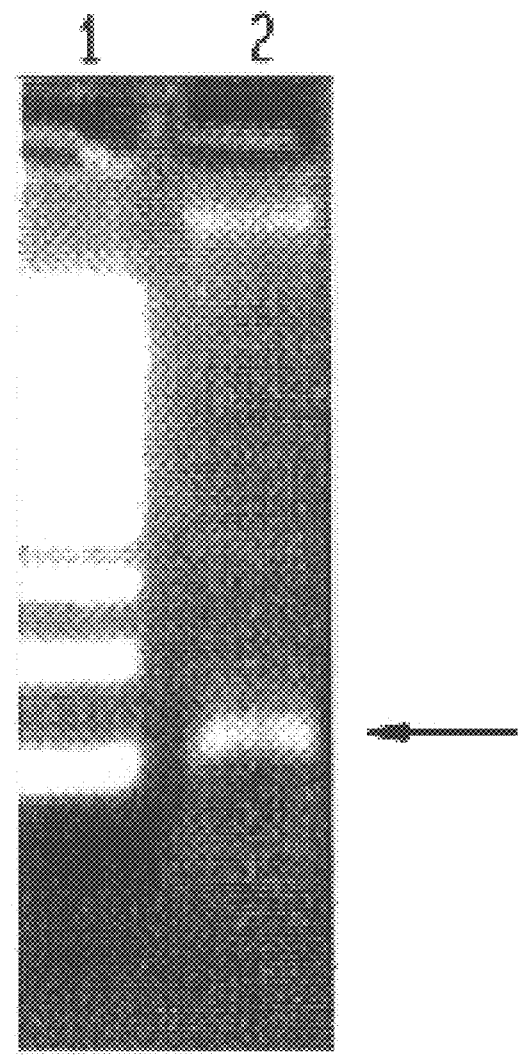
FIG. 7 shows the result of non-thio strand displacement amplification using nicking enzyme N.BstNBI. Lane 1 is the molecular weight strand and Lane 2 is the 160-bp DNA fragment produced from SDA by N.BstNBI, which is indicated by the arrow head.

4. Analyze by gel electrophoresis on high percentage agarose gels. Specific positive bands were observed on the agarose gel (FIG. 7, Lane 1=Molecular weight standard; Lane 2=160 bp band).

5. Description of primers (all flank the polylinker region of pUC19).

Primer 40:
5'-ACCGCATCGAATGCGAGTCGAGGACGACGG
CCAGTG -3' (SEQ ID NO:24)

Primer 41:
5'-CGATTCCGCAATGCGAGTCGAGGCCATGATT
ACGCCAA-3' (SEQ ID NO:25)

Bump primer #1: 5'-CAGTCACGACGTT -3' (SEQ ID NO:26)

Bump primer #2: 5'-CACAGGAAACAGC-3' (SEQ ID NO:27)

6. Description of DNA template:

The templates were constructed by cloning a short DNA duplex containing SphI site into pUC19 at EcoRI and HindIII sites to generate plasmid pUC19-SphI. Lambda DNA was digested by NlaIII and ligated into plasmid pUC19-SphI pre-digested with SphI. The DNA template, which was used to produce 160-bp DNA in SDA, was screened by PCR.

---

What is claimed is:

1. Isolated DNA coding for the N.BstNBI restriction endonuclease, wherein the isolated DNA is obtainable from ATCC Accession No. PTA-1925.

2. A vector comprising SEQ ID NO:2.

3. A host cell transformed by the vector of claim 2.

4. A method of producing an N.BstNBI restriction endonuclease comprising culturing a host cell transformed with the vector of claim 2 under conditions suitable for expression of said endonuclease.

5. Isolated DNA of claim 1, wherein the DNA comprises SEQ ID NO:2.

* * * * *

UNITED STATES PATENT AND TRADEMARK OFFICE
CERTIFICATE OF CORRECTION

PATENT NO. : 6,191,267 B1
DATED : February 20, 2001
INVENTOR(S) : Kong, et al

It is certified that error appears in the above-identified patent and that said Letters Patent is hereby corrected as shown below:

At column 7, line 20, replace "Sourcem"" with --Source™--.

At column 8, line 17, replace "16,/10" with --16/10--.

Column 9, line 16, replace "a nd" with --and--.

Column 10 line 16, replace "1.5 µl 10X X NEB #3" with
--1.5 µl 10X NEB #3--.

Column 15, line 1, replace "Primer           40:" with
--Primer 40:--.

Column 15, line 4, replace "Primer           41:" with
--Primer 41:--.

Signed and Sealed this

Twenty-ninth Day of May, 2001

Attest:

NICHOLAS P. GODICI

*Attesting Officer*          *Acting Director of the United States Patent and Trademark Office*

UNITED STATES PATENT AND TRADEMARK OFFICE
CERTIFICATE OF CORRECTION

PATENT NO. : 6,191,267 B1
DATED : February 20, 2001
INVENTOR(S) : Kong et al.

It is certified that error appears in the above-identified patent and that said Letters Patent is hereby corrected as shown below:

Column 2,
Line 37, replace "a-thio" with -- α-thio --.

Column 6,
Line 37, replace "4X10^7" with -- $4X10^{7-}$ --.

Column 7,
Line 20, replace "Sourcem"" with -- Source$^{TM}$ --.

Column 8,
Line 17, replace "16,/10" with -- 16/10 --.

Column 9,
Line 16, replace "a nd" with -- and --.

Column 10,
Line 33, replace "Quiagen" with -- Qiagen --.
Line 37, replace "1.5 µl 10X X NEB #3" with -- 1.5 µl 10X NEB #3 -- .

Column 14,
Line 17, replace "a-thio" with -- α-thio --.

Column 15,
Line 1, replace "Primer        40:" with -- Primer 40: --.
Line 4, replace "Primer        41:" with -- Primer 41: --.

Signed and Sealed this

Twenty-third Day of November, 2004

JON W. DUDAS
*Director of the United States Patent and Trademark Office*